United States Patent
Fenchel et al.

(10) Patent No.: US 9,392,958 B2
(45) Date of Patent: Jul. 19, 2016

(54) METHOD OF ATTENUATION CORRECTION OF POSITRON EMISSION TOMOGRAPHY DATA AND COMBINED POSITRON EMISSION TOMOGRAPHY AND MAGNETIC RESONANCE TOMOGRAPHY SYSTEM

(75) Inventors: Matthias Fenchel, Erlangen (DE); Kirstin Jattke, Nürnberg (DE); Jun Bao, Knoxville, TN (US); Alto Stemmer, Erlangen (DE); William Curtis Howe, Knoxville, TN (US)

(73) Assignees: SIEMENS AKTIENGESELLSCHAFT, Munich (DE); SIEMENS MEDICAL SOLUTIONS USA, INC., Malvern, PA (US)

(*) Notice: Subject to any disclaimer, the term of this patent is extended or adjusted under 35 U.S.C. 154(b) by 880 days.

(21) Appl. No.: 13/483,454

(22) Filed: May 30, 2012

(65) Prior Publication Data
US 2013/0320973 A1    Dec. 5, 2013

(51) Int. Cl.
*A61B 5/055* (2006.01)
*A61B 5/00* (2006.01)
*A61B 6/03* (2006.01)
*A61B 6/00* (2006.01)
*G01R 33/48* (2006.01)

(52) U.S. Cl.
CPC ............... *A61B 5/055* (2013.01); *A61B 5/7285* (2013.01); *A61B 6/037* (2013.01); *A61B 6/4417* (2013.01); *A61B 6/5205* (2013.01); *A61B 6/527* (2013.01); *A61B 6/5247* (2013.01); *A61B 6/5258* (2013.01); *A61B 6/5264* (2013.01); *A61B 6/5288* (2013.01); *G01R 33/481* (2013.01); *A61B 5/0035* (2013.01); *A61B 6/548* (2013.01)

(58) Field of Classification Search
CPC .... A61B 5/055; A61B 5/7285; A61B 5/0035; A61B 6/037; A61B 6/4417; A61B 6/5205; A61B 6/5247; A61B 6/5258; A61B 6/5264; A61B 6/527; A61B 6/5288; A61B 6/548; G01R 33/481
See application file for complete search history.

(56) References Cited

U.S. PATENT DOCUMENTS

| | | | | |
|---|---|---|---|---|
| 8,180,128 B2 * | 5/2012 | Feiweier | ............... | A61B 6/032 382/128 |
| 8,600,482 B2 * | 12/2013 | Schmidt | ....................... | 600/436 |
| 8,638,095 B2 * | 1/2014 | Fenchel | .................. | A61B 6/037 324/309 |
| 8,724,875 B2 * | 5/2014 | Ojha | ...................... | G01N 24/08 382/131 |
| 8,768,432 B2 * | 7/2014 | Ladebeck | .............. | A61B 5/055 324/309 |
| 8,867,814 B2 * | 10/2014 | Lonn | ..................... | G06T 11/005 382/128 |

(Continued)

FOREIGN PATENT DOCUMENTS

CN   101855564 A   10/2010
WO   WO-2009060348 A1   5/2009

OTHER PUBLICATIONS

Chinese Office action dated Aug. 4, 2015 in corresponding application No. 201310194930.0 with translation.

*Primary Examiner* — Dixomara Vargas
(74) *Attorney, Agent, or Firm* — Harness, Dickey & Pierce, P.L.C.

(57) ABSTRACT

Various embodiments relate to a method of attenuation correction of Positron Emission Tomography (PET) data based on Magnetic Resonance Tomography (MRT) data. A method of at least one embodiment further includes determining further data being indicative of an iterative cycle of a physiological observable of a patient and matching the PET data with the MRT data based on the further data.

20 Claims, 13 Drawing Sheets

(56) References Cited

U.S. PATENT DOCUMENTS

| | | | |
|---|---|---|---|
| 8,923,592 B2 * | 12/2014 | Wollenweber | A61B 5/055 382/131 |
| 8,938,280 B2 * | 1/2015 | Harvey | G01R 33/56509 600/407 |
| 8,942,445 B2 * | 1/2015 | Foo | G06T 7/0081 382/128 |
| 9,002,082 B2 * | 4/2015 | Ambwani | G01R 33/481 382/128 |
| 9,135,695 B2 * | 9/2015 | Pereira | G06T 7/0012 |
| 9,204,817 B2 * | 12/2015 | Thiruvenkadam | A61B 5/055 |
| 2008/0219510 A1 | 9/2008 | Martin et al. | |
| 2010/0268063 A1 * | 10/2010 | Schmidt | 600/411 |
| 2010/0290683 A1 | 11/2010 | Demeester et al. | |
| 2011/0044524 A1 * | 2/2011 | Wang et al. | 382/131 |
| 2011/0081067 A1 | 4/2011 | Ye et al. | |

* cited by examiner

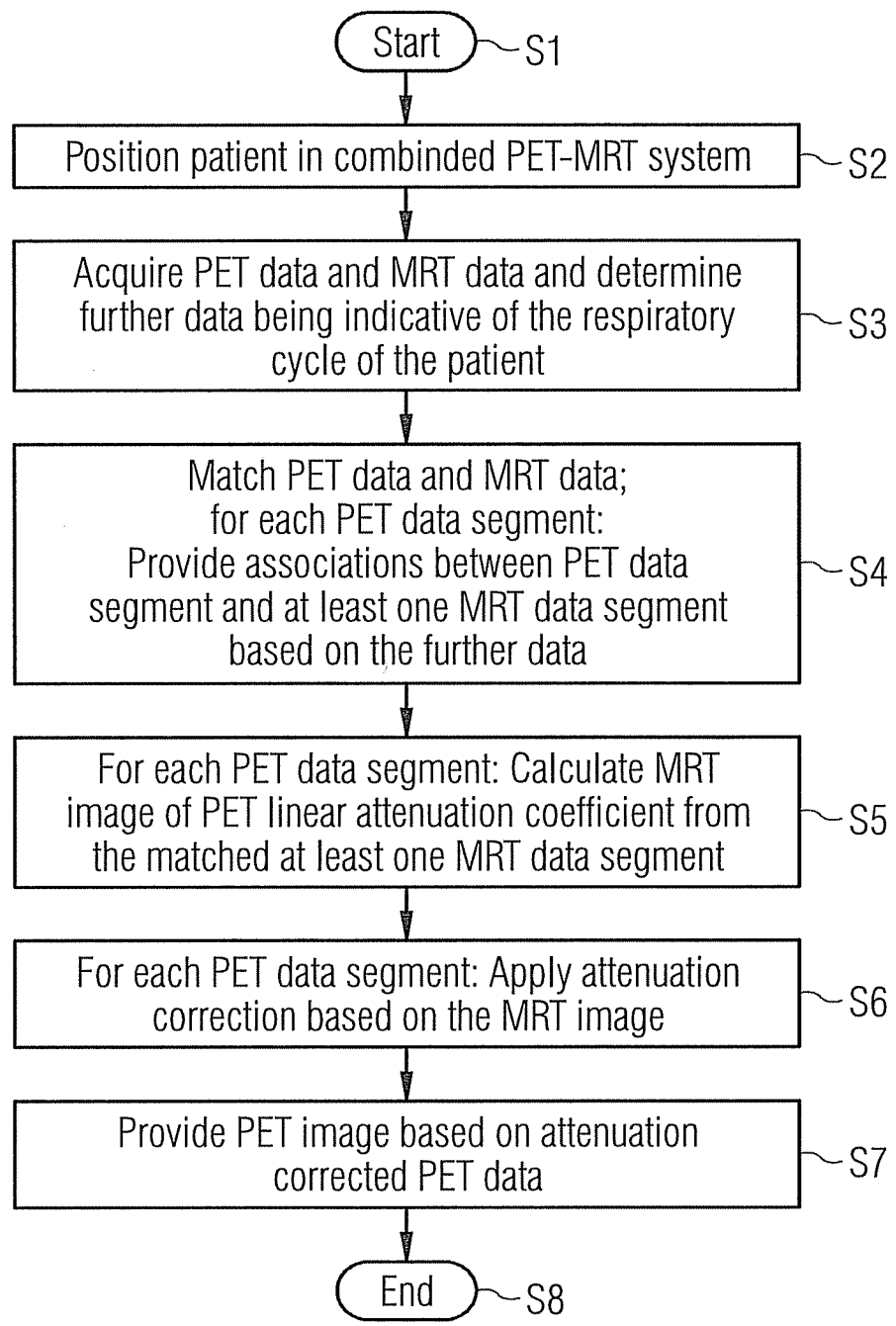

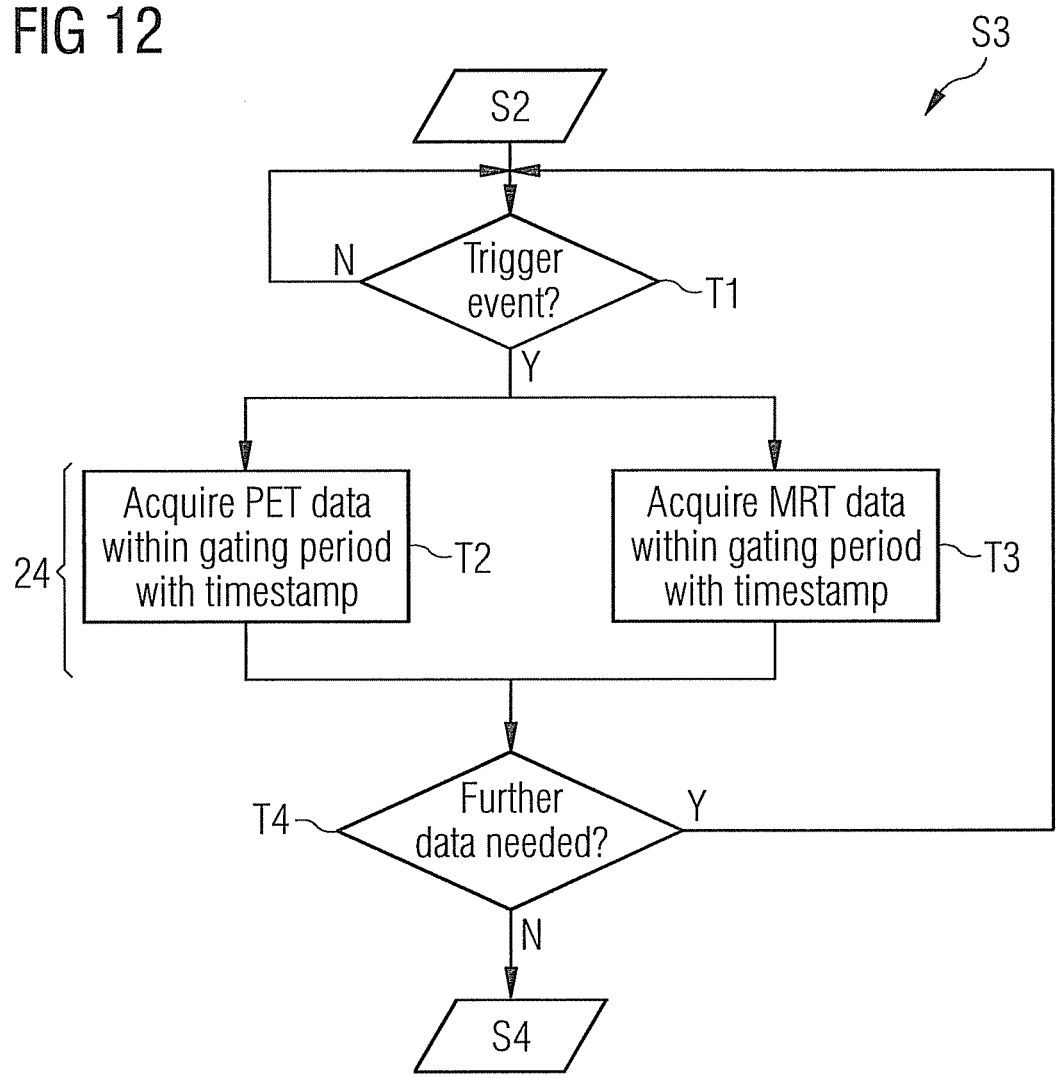

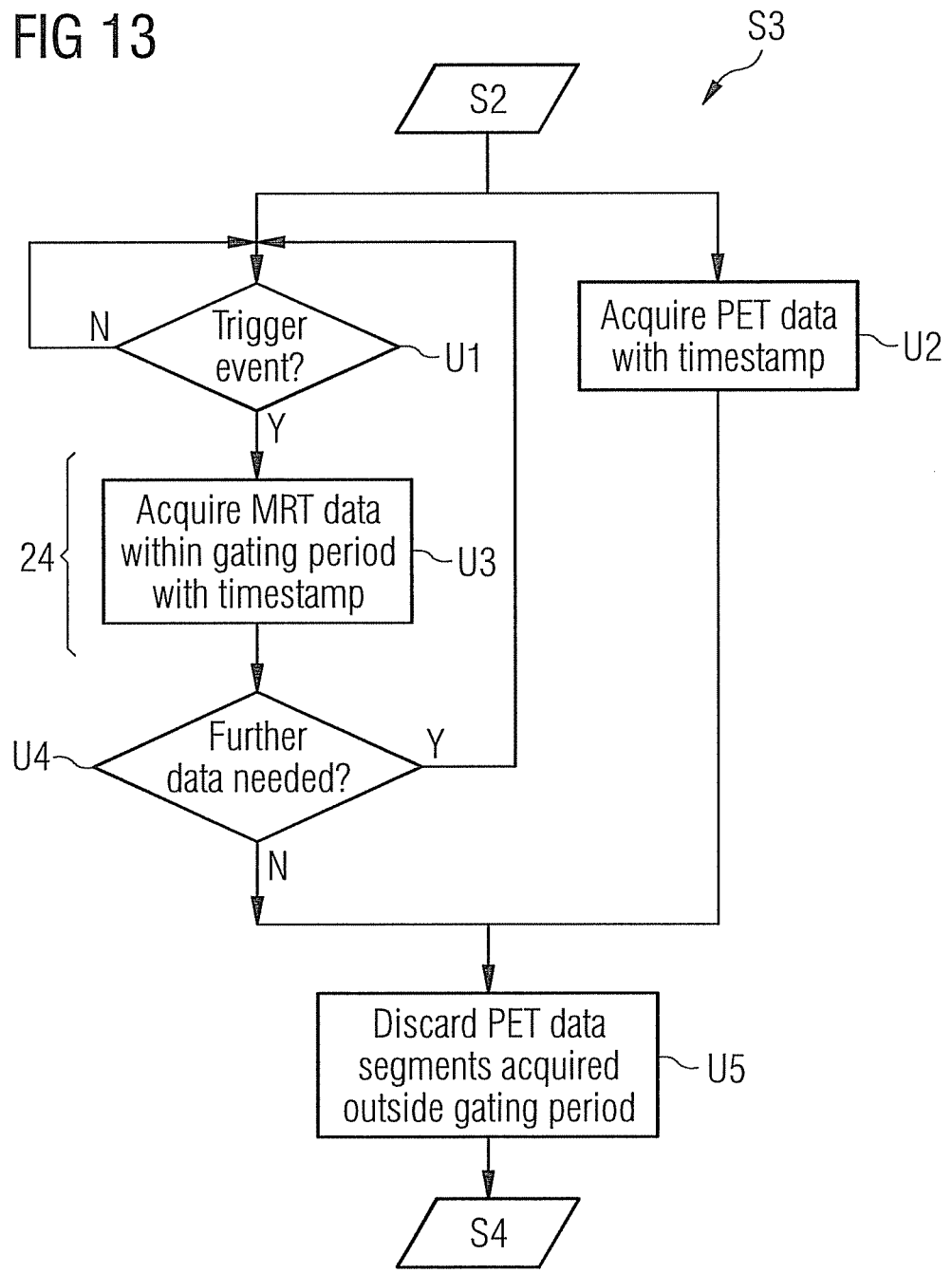

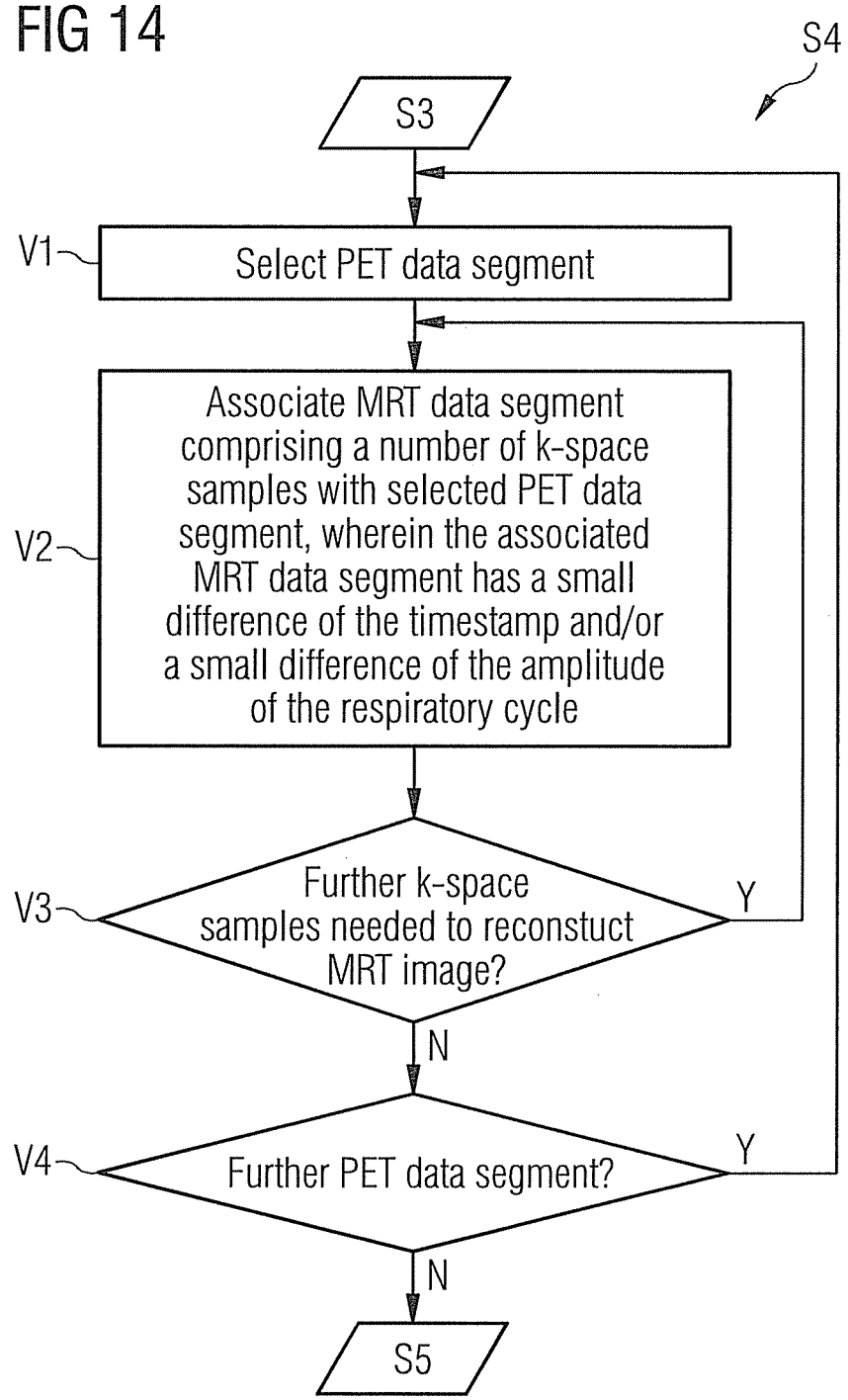

METHOD OF ATTENUATION CORRECTION OF POSITRON EMISSION TOMOGRAPHY DATA AND COMBINED POSITRON EMISSION TOMOGRAPHY AND MAGNETIC RESONANCE TOMOGRAPHY SYSTEM

FIELD

Various embodiments generally relate to a method of attenuation correction of Positron Emission Tomography (PET) data based on Magnetic Resonance Tomography (MRT) data acquired for a patient and a combined PET-MRT system. In particular, various embodiments relate to techniques to provide a matching of the PET data and the MRT data based on further data being indicative of an iterative cycle of a physiological observable of the patient, e.g., the respiratory cycle or the cardiac cycle.

BACKGROUND

In the art, techniques are known which allow employing combined PET-MRT systems to perform attenuation correction of acquired PET data based on acquired MRT data.

As part of the attenuation correction, the attenuation of PET photons, which are emitted due to an interaction of positrons and electrons, is determined for the path of the photons through absorbing tissue towards a PET detector of a PET imaging unit. The signal detected by the PET imaging unit by way of a PET detector is corrected to eliminate the determined attenuation of the PET data, i.e., PET counts (attenuation correction). Typically, the attenuation correction relies on an attenuation map (µ-map) which provides a linear attenuation coefficient (µ) or absorption value of the PET photons in a spatially resolved manner. The µ-map can be obtained from special MRT imaging sequences and post-processing techniques, such as a Dixon imaging sequence known to the skilled person. For this, MRT data is acquired which relates to the anatomy of the patient along the path of the PET photons. Therefore, MRT data is typically acquired for a region of interest to be imaged using the PET technique and additionally for a surrounding area along the path of the PET photons, i.e., which the PET photons have to cross in order to reach the PET detector of the PET imaging unit.

Generally, the accuracy of the attenuation correction of the acquired PET data may directly correlate with the signal-to-noise ratio or confidence level of a PET image which is reconstructed from the PET data. To this respect, physical values, which can be derived from the PET image or PET data, may be determined at a higher accuracy, i.e., with lower uncertainty, if attenuation correction is applied to the PET data. This may allow to achieve the technical effect of increased confidence of physical values determined from the PET data.

To this respect, in particular the breathing motion of the patient or physiological effects like cardiac motion can cause discrepancies between the PET data and the MRT data which degrade the attenuation correction. Such discrepancies may relate to a spatial mismatch and/or changes in the anatomy (lung volume, etc.). This can cause image artefacts and quantification errors which can, e.g. locally, affect the PET image quality and increase uncertainty in the derived physical values. This is in particular important for advanced and recent PET imaging techniques, like "motion freeze by gating", etc.

Various techniques are known to address such problems and will be discussed in the following.

Some techniques, such as combined PET-computer tomography (CT) techniques allow acquiring, firstly, gated PET data, and secondly and subsequently, gated CT data for the attenuation correction. In particular, the acquisition of the PET data and the CT data may occur in two independent and sequential processes separated in time. Such techniques, however, may suffer from certain disadvantages and drawbacks due to the subsequent acquisition of the CT data, either prior to or after the acquisition of the PET data. For example, such a sequential approach is problematic if the breathing pattern of the patient differs between the PET data acquisition imaging period and the CT data acquisition imaging period.

Still further techniques employ software solutions which allow a retrospective and manual matching of the PET data with the CT or MRT data by medical personnel in order to provide accurate attenuation correction. However, such techniques may be time-consuming and error-prone.

Last, techniques are known in which the MRT data for the attenuation correction is acquired in an end expiration breath hold after the acquisition of the respective PET data. The position of the diaphragm of the patient's lung is close to an average position during the free breathing at the time of PET data acquisition. In some cases, there can be differences between the anatomical position of the breathhold and the free-breathing average position. This may cause motion artefacts.

MRT is an imaging technique which allows the acquisition of two-dimensional (2D) or three-dimensional (3D) MRT images based on acquired MRT data. MRT images can picture structures and objects in the interior of a patient with comparably high spatial resolution. In MRT techniques, magnetic nuclear spins in a region of interest are aligned using a static (DC) magnetic field such that a net macroscopic magnetisation is achieved. The magnetisation is subsequently exited out of its rest or equilibrium position (typically parallel to the DC magnetic field) using radio frequency (RF) pulses. The decay of the thus excited magnetisation back to the rest position, i.e., the magnetisation dynamics of the nuclear spins, is subsequently detected using RF-detector coils. A spatial encoding/selectivity of the acquired MRT data is achieved by applying gradient fields (for slice selection, phase selection, and frequency selection). The acquired and spatially resolved MRT data are present in wave vector space (k-space) and can be transformed into image space using (inverse) Fourier transformation. By applying the gradient fields in a particular manner, it is possible to sample k-space using various trajectories, i.e., follow a certain path through the k-space during the MRT data acquisition. Such techniques are known to the skilled person, such that there is no need to discuss further details in this context.

However, such techniques employing MRT data for the attenuation correction, suffer from certain drawbacks. For example, discrepancies between the anatomical positions of the region of interest of the patient may occur between the PET and MRT data, respectively. It may not or only to a lesser degree be possible to provide matched MRT data with no or only little motion difference to the respective PET data.

SUMMARY

Accordingly, a need exists to provide advanced techniques for the attenuation correction of PET data based on MRT data. In particular, a need exists to provide techniques with decreased inaccuracies due to motion artefacts causing a discrepancy between the PET and MRT data.

The dependent claims define embodiments.

According to an aspect of at least one embodiment, a method of attenuation correction of positron emission tomography (PET) data based on magnetic resonance tomography (MRT) data using a combined PET-MRT system is provided, wherein the PET data and the MRT data are acquired for a region of interest of a patient. The method comprises acquiring the PET data for the region of interest by way of a PET imaging unit during a first imaging period, wherein the PET data comprises a plurality of PET data segments. The method further comprises acquiring the MRT data for the region of interest and a surrounding region by way of a MRT imaging unit during a second imaging period. The MRT data comprises a plurality of MRT data segments. The first and the second imaging periods at least partially overlap. The method further comprises determining, via a processor, further data being indicative of an iterative cycle of a physiological observable of the patient. The method further comprises matching, via the processor, the PET data with the MRT data, based on the further data, to provide associations between each PET data segment and at least one MRT data segment, wherein the matching provides the association between those PET and MRT data segments which are acquired during related portions of the iterative cycle. The method further comprises applying, via the processor, the attenuation correction to the PET data, wherein the attenuation correction for a given PET data segment is based on the respective associated at least one MRT data segment.

BRIEF DESCRIPTION OF THE DRAWINGS

The foregoing and additional features and effects of the invention will become apparent from the following detailed description when read in conjunction with the accompanying drawings, in which like reference numerals refer to like elements.

FIG. 11 is a flowchart of a method of attenuation correction according to various embodiments of the present invention.

FIG. 12 is a flowchart of the method of attenuation correction according to various embodiments of the present invention, wherein the acquiring of the PET and MRT data is illustrated in further detail.

FIG. 13 is a flowchart of the method of attenuation correction according to various embodiments of the present invention, wherein the acquiring of the PET and MRT data is illustrated in further detail.

FIG. 14 is a flowchart of a method of attenuation correction according to various embodiments of the present invention, wherein the matching of the PET and MRT data is illustrated in further detail.

Figure 1:
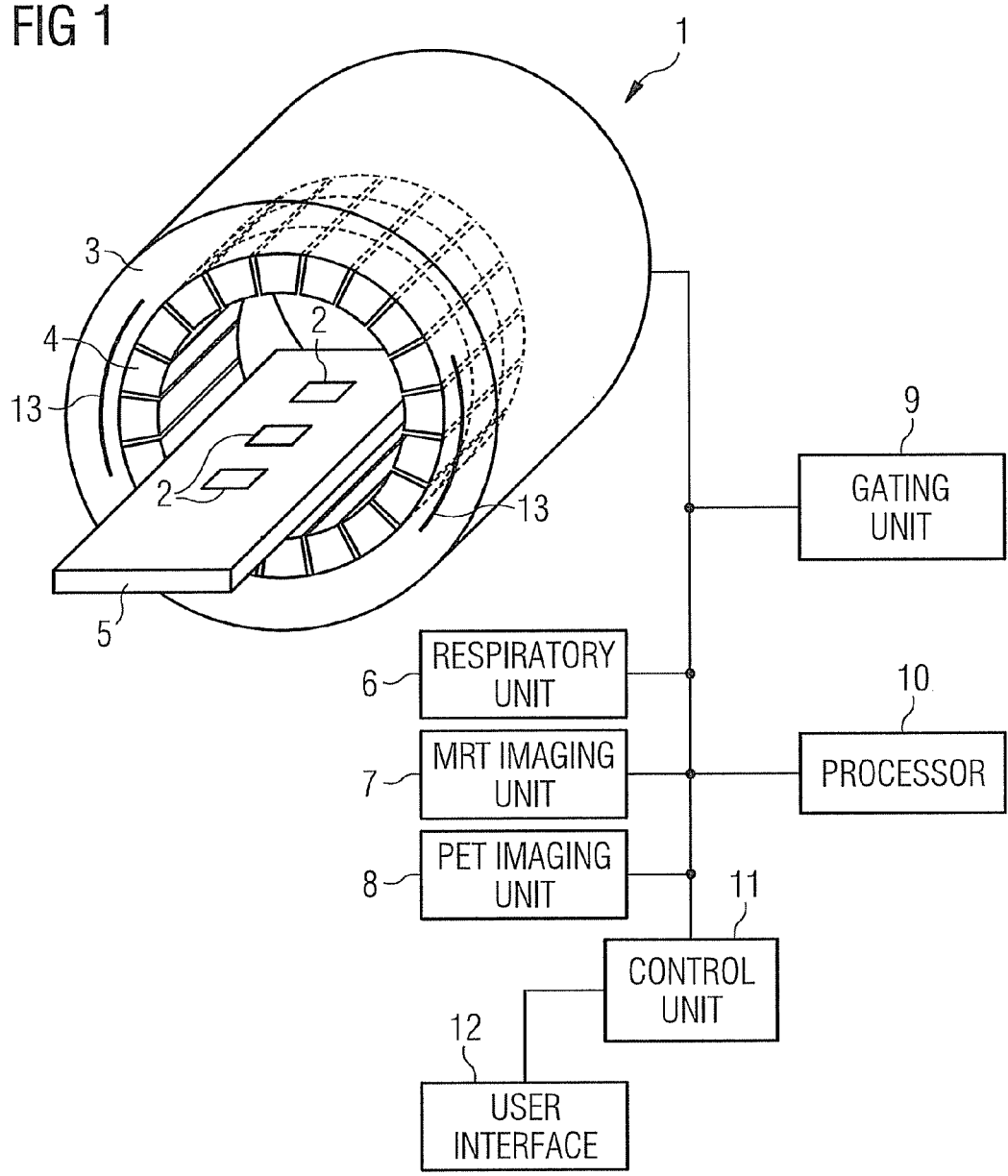
FIG. 1 is a schematic illustration of a combined PET-MRT system.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to an aspect of at least one embodiment, a method of attenuation correction of positron emission tomography (PET) data based on magnetic resonance tomography (MRT) data using a combined PET-MRT system is provided, wherein the PET data and the MRT data are acquired for a region of interest of a patient. The method comprises acquiring the PET data for the region of interest by way of a PET imaging unit during a first imaging period, wherein the PET data comprises a plurality of PET data segments. The method further comprises acquiring the MRT data for the region of interest and a surrounding region by way of a MRT imaging unit during a second imaging period. The MRT data comprises a plurality of MRT data segments. The first and the second imaging periods at least partially overlap. The method further comprises determining, via a processor, further data being indicative of an iterative cycle of a physiological observable of the patient. The method further comprises matching, via the processor, the PET data with the MRT data, based on the further data, to provide associations between each PET data segment and at least one MRT data segment, wherein the matching provides the association between those PET and MRT data segments which are acquired during related portions of the iterative cycle. The method further comprises applying, via the processor, the attenuation correction to the PET data, wherein the attenuation correction for a given PET data segment is based on the respective associated at least one MRT data segment.

For example, the first and second imaging periods may be simultaneous. For example, the iterative cycle of a physiological observable may be the patient's respiratory cycle or the patient's cardiac cycle. It is also possible that the iterative cycle of a physiological observable relates to the patient's swallowing reflex or any other cyclic observable.

The acquiring of the PET data may relate to measuring PET photons using a PET detector. To this respect, the region of interest may be the field of view of the PET-MRT system or a fraction thereof. The surrounding region may enclose the region of interest and/or border the region of interest. Also the region of interest may be a fraction of the field of view. Both the surrounding region as well as the region of interest may be positioned within an interior of the patient. The surrounding region may comprise the path of the PET photons from the region of interest towards the PET detector. The attenuation of the PET photons may occur inside the region of interest, as well as between the region of interest and the PET detector. The surrounding region and the region of interest may be connected/contiguous regions. They may be determined in the light of system parameters of the combined PET-MRT system, such as a maximum field of view, acquisition speed, etc. From an imaging point of view, the region of interest may be determined to comprise a structure, such as an organ, to be imaged.

By having the first and second imaging periods at least partially overlapping and by matching the PET and MRT data based on the further data, i.e., with respect to the iterative cycle, an increased accuracy of the attenuation correction may be achieved; this may, in turn, allow to increase the quality of PET images which are determined based on the acquired PET data. Spatial coregistration of the PET data and the attenuation map may be achieved resulting in increased local quantification accuracy. This may allow to more accurately derive physical observables, e.g., an organ volume, etc. from the PET images, i.e., with higher confidence values.

The acquiring of the PET and MRT data, the determining, the matching and the applying, as well as post-processing steps may all be performed automatically if needed.

The MRT data segments and the PET data segments may be subsets or parts of the entire MRT data and the entire PET data, respectively. For example, the MRT data segments may comprise a subset of all wave vector-space (k-space) samples or all k-space samples and the PET data segments may comprise a single PET event or a plurality of PET events. For example, the PET data segments may comprise at least one PET event. For example, the MRT data segments may comprise at least one k-space sample. For example, the PET data segments may comprise a suitable subset of all PET events. The subset of k-space samples may be suitable for the particular application. Suitable in this context may relate to the subset allowing for reconstructing a complete MRT-image, as well as the property of belonging to comparable phases of the iterative cycle. For example, "all k-space samples" may relate to all k-space samples of a particular slice or partition, i.e., with the same slice-encoding or within the same volume etc. This may depend on the MRT imaging sequence employed for the acquiring of the MRT data; in particular this may depend on the k-space trajectory employed.

In principle, the time available for sampling the k-space when acquiring the MRT data may be interrupted or intermitted as determined by analysis the further data, i.e., the iterative cycle. For example, the duration of each of the related portions of the iterative cycle, e.g., inhalation or exhalation in the case of the respiratory, may be limited. Therefore, the number of k-space samples which may be acquired without interruption within a single portion of the iterative cycle, may be limited. For example, this number of k-space samples may be referred to as MRT data segment.

Typically, the number of necessary k-space samples to provide an MRT image and the k-space trajectory and the time per k-space sample may depend on the particular MRT imaging sequence and may therefore be variable. To this respect, a particular MRT imaging sequence may be employed which enables intermitted sampling of subsets of all k-space samples, e.g., a subset of all samples having the same slice encoding. It may also be possible to employ MRT imaging sequences which allow for rapid k-space sampling, e.g., using partial parallel acquisition (PPA) techniques, such as "Generalized Auto-Calibrating Partial Parallel Acquisition" (GRAPPA), "Sensitivity Encoding" (SENSE), or "Simultaneous Acquisition of Spatial Harmonics" (SMASH). By using such accelerated techniques, which may undersample the k-space and reconstruct missing samples, it may be possible to rapidly sample the k-space within comparably shorter time, such that the MRT data segments may correspond to all k-space samples which have, e.g., the same slice encoding. However, in a preferred embodiment, the subset may be smaller than the complete k-space, e.g., for a certain slice-selection gradient, such that repeated acquisition and later selection of the suitable MRT data segments by correlating with the further data, may become necessary.

It should be understood that particular MRT imaging sequences may be employed which allow determining of the μ-map based on the acquired MRT data. A typical sequence known to the skilled person is the Dixon imaging sequence. Such MRT imaging sequences or related imaging sequences and suitable post-processing techniques may allow for spatially segmenting the acquired MRT data into portions corresponding to different linear attenuation coefficients, i.e., having different numerical values of the respective entries of the μ-map. For example, a classification may relate to fat/soft tissue/lung and air. Finer segmentation or coarser segmentation is also possible.

Therefore, the MRT imaging sequence may allow for full 3D coverage of the region of interest and the surrounding region, i.e., the entire object, with sufficient spatial integrity and reproducible fat and soft tissue contrast for inline segmentation of the aforementioned tissue classes. Inline segmentation may refer to automatically and directly subsequently to the acquiring performing the segmentation.

The related portions of the iterative cycle may have related phases of the iterative cycle and/or related amplitudes of the iterative cycle. For example, the related phases may correspond to the inhalation phase or the exhalation phase of the patient's respiratory cycle. The amplitude may correspond to a volume of air inhaled or exhaled by the patient. As the breathing pattern may change over time, the amplitude and/or frequency of the respiratory cycle may be a function of time as well.

In this light, the related portions of the iterative cycle may correspond to portions having substantially the same amplitudes of the iterative cycle and/or having substantially the same phases of the iterative cycle. A threshold comparison may allow deviations to a certain degree, e.g., provide a tolerance range or acceptance window.

Various embodiments are conceivable which allow for providing the associations in view of the amplitude and/or phase of the iterative cycle. Some embodiments may employ gating techniques as set forth below.

The method may further comprise gating of the PET data and the MRT data, based on the determined further data, to particular phases of the iterative cycle by way of a gating unit such that the associated PET data segments and MRT data segments may be acquired during related phases of the iterative cycle.

For example, the gating unit may be a separate unit or may be implemented as part of the processor or the MRT imaging unit, either as hardware or software or a combination thereof. Gating, in general, may correspond to selectively acquiring and/or processing of the MRT and PET data depending on the iterative cycle, i.e., the further data. Various gating techniques are conceivable, such as self-gating, e.g., based on the MRT data, retrospective gating or prospective gating, i.e., gating either at the time of MRT and PET data acquisition or gating sometime after MRT and PET data acquisition, e.g., by selectively discarding of those previously acquired data segments which are outside gating periods. In the case of the iterative cycle corresponding to the respiratory cycle, the gating periods of the gating may relate to the inhalation or exhalation phases.

The determining of the further data may further comprise repeatedly measuring, during the first imaging period and the second imaging period, the further data. For example, an additional respiratory unit may be provided, such as a breathing sensor. Such devices which are known to the skilled person can be placed in contact with the patient and repeatedly measure, e.g., the amplitude of lung motion or other respective observables, in order to provide the further data being indicative of the respiratory cycle.

It should be understood that in various embodiments where the further data is indicative of the physiologic observable other than the respiratory cycle, respective other device(s) for measuring the further data are known to the skilled person. For example, blood pressure sensors or electrocardiograms are known for measuring the cardiac cycle, e.g., by way of a cardiac unit.

In various further embodiments, the further data may also be navigator MRT data and may be measured by the MRT imaging unit in between two subsequent MRT data segments. For example, in the case of the respiratory cycle, the navigator MRT data may be indicative of a motion of the lung of the patient. For example, the navigator MRT data may image a significant portion of the diaphragm of the patient. The navigator MRT data may be of comparably low spatial resolution (in particular if compared to the MRT data) and therefore may be rapidly acquired during comparably short measuring time periods. In other words, the measuring of the navigator MRT data may be interleaved with the measuring of the MRT data used for the attenuation correction. For example, the navigator MRT data may be measured in fixed time intervals, e.g., at a fixed repetition rate, or may be measured whenever MRT data acquisition of a particular MRT data segment is completed. By measuring the further data using the MRT imaging unit, a particularly simple method of attenuation correction may be achieved—in particular, it may be possible to rely on the already present MRT imaging unit, rather than providing an additional respiratory unit.

In various further embodiments, it may be possible that the determining of the further data comprises obtaining the further data from the MRT data to obtain self-gated PET and MRT data. It may be possible that the MRT data itself is indicative of the iterative cycle of the patient. In such an embodiment, it may be possible to derive the further data from the already present MRT data without having to provision any external respiratory unit or cardiac unit or other respective device(s). Whether the MRT data is indicative of, e.g., the respiratory cycle may depend on the position of the region of interest within the patient.

In various embodiments, the gating may comprise retrospectively and selectively discarding of the PET data segments and the MRT data segments which are acquired outside gating periods. The gating period may relate to the time period during which a gating criterion is fulfilled, e.g., during which the phase of the iterative cycle lies within the range of acceptable values. Therefore, the gating period may, in a simple embodiment, relate to the inhalation phase of the respiratory cycle or may relate to the exhalation phase of the respiratory cycle. By retrospectively and selectively discarding of the PET and MRT data segments, it may be possible to employ a comparably simple data acquisition scheme. In particular, at the time of the data acquisition, it may not be necessary to consider the further data, e.g., in real time or on-the-fly. It may rather be possible to consider the further data only after the data acquisition has completed.

To this respect, particular MRT imaging sequences may be employed which provide redundancy in the acquired MRT data. For example, one and the same MRT data segment may, i.e. containing the same k-space samples, may be acquired multiple times in a way to provide a high statistical likelihood that even after the retrospectively selectively discarding of those MRT data segments which are located outside the gating periods, the k-space is fully sampled. In the same manner, the acquiring of the PET data may be performed for a comparably longer first imaging period such that it may be ensured that sufficient PET events are obtained even in view of selectively discarding those PET data segments which are acquired outside the gating periods. In other words, the PET integration time, i.e., a duration of the first imaging period, may be chosen long enough such that redundancy in the acquired PET data exists and the derived PET image has a sufficient signal-to-noise ratio.

Therefore, as set forth above, various embodiments may rely on various techniques for determining the further data:

the determining may comprise dedicated measurements, e.g., using the respiratory unit or the MRT imaging unit, or may comprise obtaining the further data from the MRT data used for the attenuation correction. Combinations are possible; the method of attenuation correction may then further comprise averaging of the measured and/or obtained further data of the different sources. In any case, flexibility exists in the selection of the appropriate device(s) to determine the further data. Flexibility also exists in the gating which is based on the further data, as will be set forth below.

In various embodiments, the gating may comprise prospectively enabling the acquiring of the MRT data and the PET data during gating periods, wherein the acquisition of the MRT data yields a predefined number of k-space samples as MRT data segments during each gating period. Such prospective gating may allow to only acquire the MRT data and the PET data during the gating periods determined by the gating unit. In particular, it may not be necessary to retrospectively and selectively discard certain MRT and/or PET data segments—although it may be possible to combine prospective and retrospective gating schemes in various embodiments.

In the case of prospective gating, the gating unit may, e.g., send a control signal to the PET imaging unit and the MRT imaging unit which is indicative of the gating periods. The control signal may signal a trigger event relating to, e.g., the beginning or the end of a gating period. To this respect, the MRT imaging sequence yielding the MRT data may be adapted appropriately to ensure that the predefined number of k-space samples per MRT data segment may be completely acquired during each gating period; e.g., a gating period may have a specified minimum duration, which may be derived from the historical or previously measured breathing pattern of the patient's respiratory cycle. For example, a k-space resolution or an acceleration factor in the case of a PPA imaging sequence may be adapted accordingly such that the predefined number of k-space samples may be acquired. The predefined number of k-space samples may, e.g., relate to a given subset of all k-space samples having the same slice encoding or may relate to all k-space samples with the same slice encoding. By providing the predefined number of k-space samples during each gating period, a deterministic and fully controllable acquisition of the MRT data may be implemented.

The gating may comprise a semi-prospective gating scheme.

In the semi-prospective gating scheme, the acquiring of the MRT data may comprise: repeatedly acquiring a given MRT data segment and repeatedly acquiring a further MRT data segment in response a trigger event determined from the further data and being indicative of a completed iterative cycle period.

In one example, irrespective of the particular phase of the iterative cycle, at least one k-space sample of the given MRT data segment is repeatedly acquired. Sometime after the acquiring, this repeatedly acquired given MRT data segment (relating to the same at least one k-space sample) is partly selectively discarded depending on which comprised k-space samples were acquired outside a gating period. These steps may be referred to as the retrospective steps of the semi-prospective gating scheme.

The repeated acquiring of the further MRT data segment may be triggered by a certain phase of the iterative cycle. I.e., the semi-prospective gating scheme moves to the next MRT data segment whenever it is determined from the further data that a complete cycle or period of the iterative cycle is completed. By such device(s), it may be ensured that all required k-space samples for reconstructing a complete MRT image are successfully acquired.

The foregoing features may be employed to facilitate the matching with respect to related phases of the iterative cycle. By gating to a certain phase of the patient's iterative cycle, the matching to this certain phase may be readily and inherently achieved as all available MRT and PET data segments relate to the same phase. Additionally or instead of the matching with respect to related phases, the matching may be employed with respect to certain amplitudes of the iterative cycle. For example, as the patient's breathing pattern may be subject to a time dependence, it may be desired to provide the associations between those PET and MRT data segments which have comparable amplitudes of the respiratory cycle, i.e., both lying within a tolerance range or acceptance window. Various embodiments providing such effects will be discussed in the following.

In various embodiments, the second imaging period may be a fraction of the first imaging period and each PET data segment may be provided with a timestamp being indicative of the time of the acquiring of the respective PET data segment. Each MRT data segment may be provided with a timestamp being indicative of a time of the acquiring of the respective MRT data segment. The matching may provide the associations between the PET and MRT data segments based on a difference of the respective timestamps such that the associated PET and MRT data segments have the related amplitudes of the iterative cycle.

For example and with respect to the respiratory cycle, the patient's breathing pattern, in particular the amplitude of the respiratory cycle, may change continuously and steadily on a certain characteristic time scale. This characteristic time scale may be longer than a period of the respiratory cycle. The patient's breathing pattern may, in other words, change slowly in time if compared with a single breath hold. This characteristic time scale may in particular relate to a plurality of full periods of the respiratory cycle, i.e., relate to 5 or 10 or 20 or 50 or even more breathing cycles, depending on the patient. In other words, the typical time scale may be on the order of tens of seconds or minutes or tens of minutes. Such a time scale may be significantly longer than the typical time difference two subsequent portions of the respiratory cycle with the same phases, i.e. in various embodiments between two subsequently acquired PET data segments and/or two subsequently acquired MRT data segments. In the same manner, the parameters of the cardiac cycle may change, e.g., the blood pressure may rise or fall and the heartbeat may become faster or slow down. In such a case, it may be possible to provide matching with respect to substantially equal amplitudes of the iterative cycle by considering the difference of the respective timestamps of the acquiring of the PET and MRT data segments. The matching may provide the associations between the PET and MRT data segments based on a small difference of the respective timestamps.

For example, the matching may provide the associations between those PET and MRT data segments having a minimized difference of the respective timestamps under the constraint of related phases of the iterative cycle. Namely, in a simple embodiment, by providing the association between those PET and MRT data segments which are, in other words, neighbouring in time-space, comparable amplitudes of the iterative cycle may be achieved. In such a case, it may not be necessary to provide any data analysis of the further data in order to explicitly determine the particular amplitude of the iterative cycle—rather, it may be sufficient that the matching provides the associations between those PET and MRT data segments having a minimized or minimum difference of the respective timestamps. This may allow for a particular simple implementation of the matching.

For example, the constraint of related phases of the iterative cycle may be fulfilled by way of the gated acquisition. When employing the gating as above, the constraint of related phases of the iterative cycle may be fulfilled inherently.

In various embodiments, the method of attenuation correction may further comprise determining the amplitudes of the iterative cycle based on the further data. The matching may provide the associations between those PET and MRT data segments having a minimized difference of the respective amplitudes of the iterative cycle under the constraint of related phases of the iterative cycle. Namely, it may also be possible to analyze the further data in order to explicitly determine the amplitudes of the iterative cycle. For example in the case of the respiratory cycle, when measuring navigator MRT data, quantitative indications of the motion of the lung may be determined, e.g., from the position variation of the patient's diaphragm, and from this information the amplitudes of the respiratory cycle may be derived. Similar techniques are possible using the external respiratory unit, such as the breathing sensor. The same may apply to the cardiac cycle when imaging the heart using an external cardiac unit. Also, in the self-gated techniques quantitative information on the iterative cycle may be determined. While such techniques may require comparably complex processing of the further data, they may allow an increased accuracy of the matching and therefore may result in an increased accuracy of the attenuation correction.

Furthermore, an increased flexibility in the matching may be achieved. Namely, while in various embodiments it may be necessary to iteratively and continuously acquire MRT data segments in order to realize a sufficiently small difference of the respective timestamps between the PET and MRT data segments to ensure comparable amplitudes of the iterative cycle, when determining the amplitudes of the iterative cycle from the further data, it may be possible to have a larger difference between the time of acquisition of matched PET and MRT data segments. Namely, by determining the amplitudes of the iterative cycle, e.g., along with the phases of the iterative cycle, all characteristic parameters of the iterative cycle may be known to the system such that the matching can also provide the associations between PET and MRT data segments having a large difference of the time of the acquiring, e.g., having a large difference between the respective timestamps. In particular, in such an embodiment, it may not even be necessary to provide the timestamps for the acquiring of each PET and MRT data segment. The matching may rely solely on the further data.

Above, various embodiments have been illustrated which relate to techniques for the matching of the PET and MRT data segments in view of the iterative cycle. By such device(s), it may be ensured that the characteristic parameters of the iterative cycle, i.e., the phase and amplitude, may be substantially equal in the PET and MRT data segments between which the matching provides the associations. Compensation for temporal variations in the characteristic parameters of the iterative cycle may be achieved. In other words, the matching has been discussed in view of the parameters of the iterative cycle.

However, it should be understood that the matching may also fulfil the requirement that for each PET data segments associations to a sufficient number of MRT data segments is provided, i.e., that from the at least one obtained or MRT data segment being associated with a given PET data segment a MRT image can be calculated. In other words, associations to a number of MRT data segments which are sufficiently sampling the k-space may be provided by the matching.

In various embodiments, the matching may provide the associations such that a MRT image can be calculated from the associated at least one MRT data segment. The matching may further comprise calculating the MRT image from the associated at least one MRT data segment. The MRT image may provide a segmentation of the region of interest and the surrounding region based on PET attenuation values and the applying of the attenuation correction may be based on the PET linear attenuation coefficients.

Therefore, from the MRT image the $\mu$-map of the PET linear attenuation coefficient may be derived. For example, the $\mu$-map may comprise the segmentation with respect to three or four or five different PET linear attenuation coefficient values, e.g., selected from the group consisting of: fat, soft tissue, lung, and air.

The requirement of being able to calculate the MRT image from the associated MRT data segments may be fulfilled in numerous ways. In particular, the acquiring of the MRT data may be configured to this respect.

For example, the acquiring of the MRT data may repeatedly sample the region of interest and the surrounding region for a predefined plurality of iterations and/or using a statistical sequence.

Namely, be repeatedly sampling for a plurality of times, redundancy of the available MRT data may allow the matching to fulfil both requirements, i.e., with respect to the related portions of the iterative cycle, as well with respect to the sufficient number of k-space samples. In other words, by having redundant MRT data available, the likelihood for obtaining all k-space samples for a given amplitude and phase of the iterative cycle may be increased.

Similar effects may be achieved for the statistically sampling. E.g., in case of retrospective gating, certain k-space samples may be selectively discarded. However, if the sampling is statistical, it may be possible to employ statistical methods in order to predict or estimate the number of k-space samples necessary to ensure successful reconstruction of the MRT image.

In case of prospective gating, the MRT imaging sequence may, in various embodiments, acquire all k-space samples having the same slice selection during a single gating period. Then the MRT image may always be reconstructed from a single MRT data segment. Such an embodiment may have certain advantages with respect to statistics and stability. However, similar argumentations apply if the MRT imaging sequence only acquires a subset of all k-space samples having the same slice selection during a single gating period, e.g., one half of the k-space etc. Here, the matching may provide the associations always with respect to two MRT data segments.

The method may further comprise acquiring further MRT data for a diagnostic application during a third imaging period by way of the MRT imaging unit, the third imaging period being a fraction of the first imaging period and being complementary to the second imaging period. Typically, the acquiring of the MRT data for the attenuation correction may only require a comparably shorter second imaging period if compared to the first imaging period of the acquiring of the PET data. In other words, the integration time needed to obtain a full set of PET data segments may be comparably longer then the integration time needed to obtain a full set of MRT data segments. Therefore, it may be possible to acquire the further MRT data to obtain a better MRT-image for the attenuation correction post-processing.

In various embodiments, the second imaging period may be arranged in the beginning and the end of the first imaging period, and the third imaging period may be arranged in between the two parts of the second imaging period. In other words, the MRT data used for the attenuation correction may be achieved in the beginning and the end of the acquiring of the PET data; while in between the further MRT data may be acquired. In other words, the first and/or second and/or third imaging periods may be intermitted.

According to the aforementioned techniques and various embodiments of the method of attenuation correction, an optimally corrected PET image may be reconstructed from the PET data and a result of a precisely matched attenuation map or µ-map of the linear attenuation coefficient. Accurate matching may be ensured by identical and simultaneous gating for both the MRT data acquisition and the PET data acquisition. For example, in a clinic application, the benefits may include high accuracy and fewer artefacts in certain areas of the patient, such as lung, liver, and diaphragm. Consequently, the PET images may be more accurate in terms of subsequent quantification and may improve the diagnostic value.

According to a further aspect, a combined PET-MRT system for acquiring, for a region of interest of a patient, MRT data and PET data and for providing attenuation correction of the PET data based on the MRT data is provided. The combined PET-MRT system comprises a PET imaging unit being configured to acquire the PET data for the region of interest during a first imaging period, the PET data comprising a plurality of PET data segments. The combined PET-MRT system further comprises a MRT imaging unit being configured to acquire the MRT data for the region of interest and a surrounding region during a second imaging period, the MRT data comprising a plurality of MRT data segments, wherein the first and second imaging periods at least partially overlap. The combined PET-MRT system further comprises a processor being configured to perform the following steps: determining further data being indicative of an iterative cycle of a physiological observable of the patient; and matching the PET data with the MRT data, based on the further data, to provide associations between each PET data segment and at least one MRT data segment, the matching providing the associations between those PET and MRT data segments which are acquired during related portions of the iterative cycle; and applying the attenuation correction to the PET data, wherein the attenuation correction for a given PET data segment is based on the respective associated at least one MRT data segment.

In particular the combined PET-MRT system may be configured to perform a method of attenuation correction according to a further aspect of an embodiment of the invention.

For such a combined PET-MRT system, effects may be obtained which are comparable to, the effects which may be obtained with the method of attenuation correction according to the further aspect as set forth above.

It is to be understood that the features mentioned above and features yet to be explained below can be used not only in the respective combinations indicated, but also in other combinations or in isolation, without departing from the scope of the present invention. Features of the above-mentioned aspects and embodiments may be combined with each other in other embodiments. For example, features relating to techniques providing the associations with respect to related amplitudes of the iterative cycle may be combined with features relating to techniques providing the associations with respect to related phases of the iterative cycle. However, combining these two techniques may not be necessary—features relating to each technique may also be applied in isolation.

In the following, embodiments of the invention will be described in detail with reference to the accompanying drawings in which like numerals reference like elements. It is to be understood that the following description of embodiments is not to be taken in a limiting sense. The scope of the invention is not intended to be limited by the embodiments described hereinafter or by the drawings, which are taken to be illustrative only.

FIG. 1 is a schematic illustration of a combined PET-MRT system 1. A patient may be placed on a table 5 and positioned inside a magnet 3. The magnet 3 can apply a static (DC) magnetic field of a few Tesla in order to align nuclear spins. The magnet 3 may comprise superconducting coils in liquid Helium.

A PET imaging unit 8 and a PET detector 4 are provided; they are configured to acquire PET data. The PET detector measures coincident PET photons and the PET imaging unit 8 provides the PET data based on these measurements. Details of an operation of the PET components 4, 8 are known to the skilled person such that there is no need to discuss further details in this context.

A MRT imaging unit 7 and a MRT detector 2 are configured to operate according to certain MRT imaging sequences and to provide MRT data. The MRT detector 2 comprises RF coils for detection of the magnetization dynamics of the nuclear spins; gradient coils 13 for spatial encoding of the MRT data via gradient fields are provided. The MRT imaging unit 7 reads out the signal of the MRT detector 2 to provide the MRT data. The operation of the MRT components 2, 7, 13 as a MRT apparatus are known to the skilled person such that there is no need to discuss further details in this context.

In particular, the MRT imaging unit 7 is configured to provide the MRT data such that it is indicative of a linear attenuation coefficient of the PET photons. This may be achieved by respective MRT imaging sequences, e.g., a Dixon sequence or related sequences. Then, the MRT data can be used by a processor 10 in order to calculate an attenuation correction of the PET data, e.g., in the form of a map of the linear attenuation coefficient value or µ-map. The processor 10 is configured to apply the attenuation correction to the PET data.

In order to apply the attenuation correction with high accuracy, i.e., with small errors, the processor 10 is further configured to determine further data being indicative of an iterative cycle of a physiological observable of a patient, e.g., the respiratory cycle of the patient, or the cardiac cycle or the cycle relating to the swallowing reflex. In the following, reference will be made predominantly to the respiratory cycle. However, it should be understood that respective embodiments may be implemented with respect to other cyclic physiological observables.

The processor 10 is furthermore configured to match the MRT data of the MRT imaging unit 7 with the PET data of the PET imaging unit 8 based on the further data. This enables to apply the attenuation correction for each PET data segment, e.g., each PET event (coincident PET photons), using such MRT data which is acquired at times where the respiratory cycle has substantially equal characteristic parameters (phase and amplitude) as at the time of the acquiring of the PET event. In other words, the matching may provide associations between each PET data segment and at least one MRT data segment, wherein the matching provides the associations between those PET and MRT data segments which are acquired during related portions of the respiratory cycle.

Figure 2:
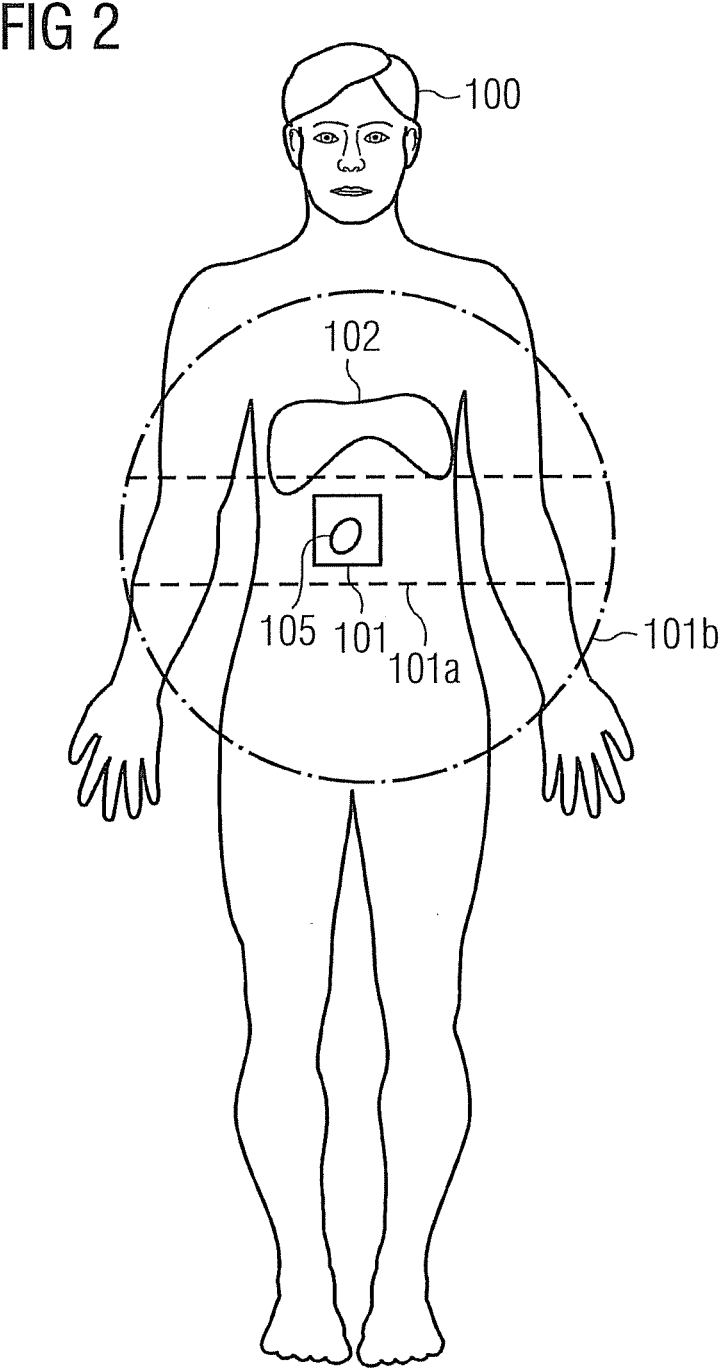
FIG. 2 illustrates a region of interest and a surrounding region of a patient subject to imaging using the combined PET-MRT system of FIG. 1.

Turning to FIG. 2, in order to apply the attenuation correction with sufficient accuracy, the MRT data is acquired for a region of interest 101 for which the PET data is also acquired. The region of interest 101 can comprise, e.g., an organ 105 which should be comprised in a PET image obtained from the PET data. Furthermore, the patient's 100 diaphragm 102 is illustrated in FIG. 2. As the pairs of PET photons originating from the region of interest 101 have to travel through the patient 100 to reach the PET detector 4, the attenuation value is also determined for a surrounding region 101a which is a connected region bordering to the region of interest 101. In FIG. 2, the surrounding region 101a is indicated using a dashed line. Both, the region of interest 101 and the surrounding region 101a are situated within a field of view 101b (dashed-dotted line in FIG. 2) of the combined PET-MRT system 1. The field of view 101b may be limited by the design of the combined PET-MRT system 1.

Figure 4:
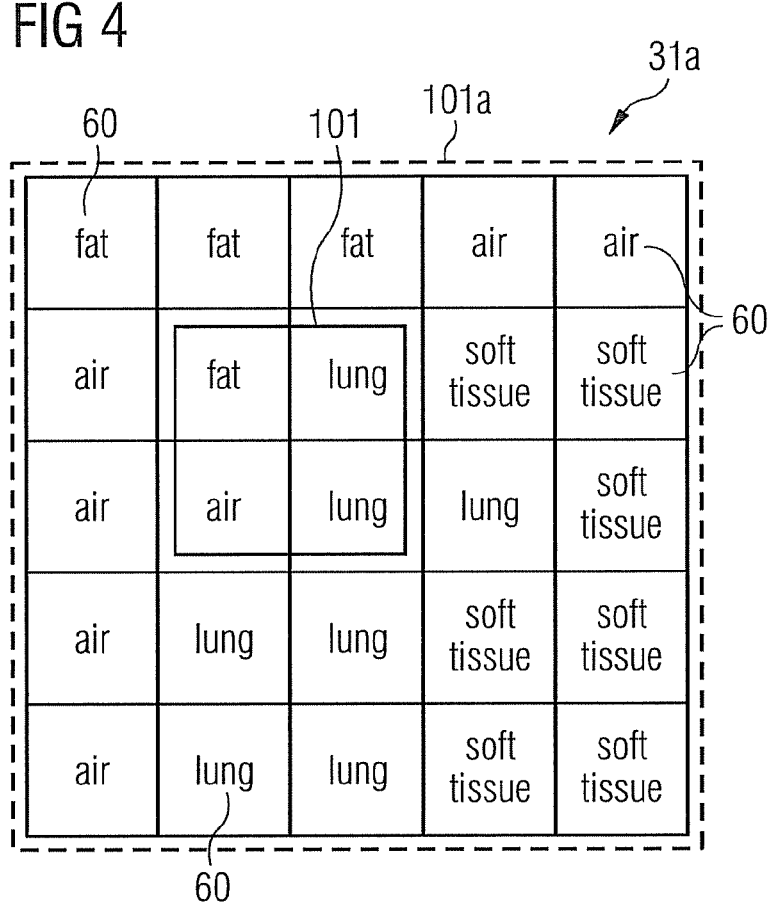
FIG. 4 illustrates an MRT image and attenuation map obtained from MRT data acquired with the combined PET-MRT system of FIG. 1.

In FIG. 4, the MRT image 31a obtained from the MRT data is schematically illustrated; e.g., FIG. 4 corresponds to a 2d slice obtained using a given slice-encoding gradient field by way of the gradient coils 13. It should be understood that multiple such MRT images 31a can be provided to provide a 3d or multi-slice attenuation correction. The MRT image 31a corresponds to a parameter map of the attenuation value 60, i.e., a μ-map. In the example of FIG. 4, four classes of segmentation, namely fat—air—soft tissue—lung, are provided; these classes are associated with different numerical values for the attenuation value 60 which are known to the skilled person. Other classifications are possible. The MRT image 31a covers the region of interest 101 (full line), as well as the surrounding region 101a (dashed line). Therefore, the MRT image 31a provides a segmentation of the region of interest 101 and the surrounding region 101a based on the PET attenuation value 60.

Turning back to FIG. 1, the components as discussed above can be controlled by way of a control unit 11. The control unit 11 is connected to the various units and devices via communication links and can drive the devices via control commands and/or received data. Connected to the control unit 11 is further a user interface 12, e.g., in the form of a keyboard and/or a monitor and/or a touchscreen and/or voice control and/or remote control.

The control unit 11 can be provided in the combined PET-MRT system 1, but can also be configured such that it can be connected to the combined PET-MRT system 1 externally and thus via an interface. In particular, the control unit 11 is configured such to transmit control commands and/or information relating to a timing or triggering of the different units. In particular, the control unit 11 is configured to synchronize the acquiring of the PET data and the acquiring of the MRT data with respect to the related portions of the patient's respiratory cycle. Furthermore, the control unit 11 is configured to synchronize the determining of the further data being indicative of the respiratory cycle.

In particular, the control unit 11 can control the timing of PET and MRT data acquisition such that the acquiring of the PET data is performed by the PET imaging unit 8 during a first imaging period, while the acquiring of the MRT data is performed by the MRT imaging unit 7 during a second imaging period, wherein the first and second imaging periods at least partially overlap. In other words, PET and MRT data acquisition can be synchronized by the combined PET-MRT system. It should be understood that the combined PET-MRT system 1 is configured to allow parallel operation of the MRT detector 2 and the PET detector 4. Different synchronization schemes, i.e., different temporal alignments of the first and second imaging periods will be discussed hereinafter with respect to the FIGS. 5-8.

According to various embodiments, the at least partially synchronized acquiring is advantageously employed for the attenuation correction. For this, the matching between the PET data and the MRT data is executed by the processor 100. The matching will be explained in further detail below.

The PET data comprises a plurality of individual PET data segments. For example, a single PET data segment may correspond to a single PET event, i.e., the detection of a pair of coincident PET photons by the PET detector 4, or may correspond to a set of PET events, e.g., in rapid temporal succession or in close spatial proximity.

Figure 3:
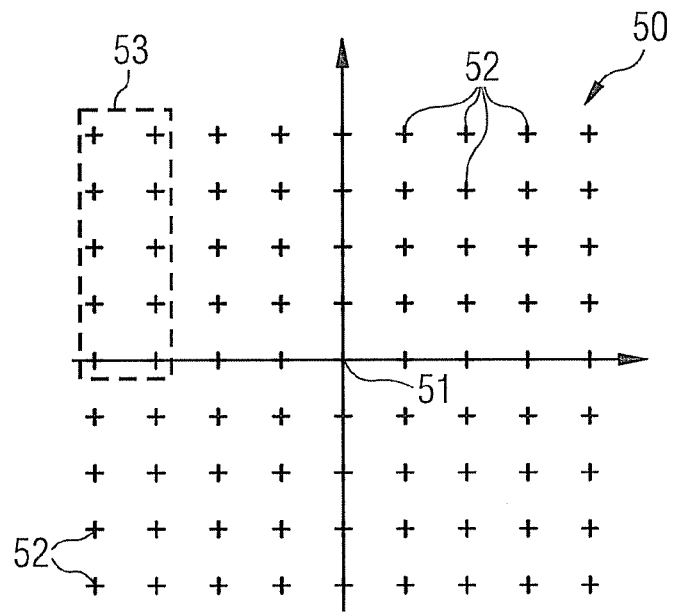
FIG. 3 illustrates the k-space and samples of the k-space with respect to MRT imaging sequences.

Likewise, the MRT data comprises a plurality of individual MRT data segments. For this, reference is made to FIG. 3. FIG. 3 illustrates the samples 52 of the MRT data in k-space 50; a k-space center 51 is also shown relating to zero wave vector (infinite wavelength). A single slice is shown, i.e., all samples 52 in FIG. 3 have the same slice encoding. A set of such samples 52 corresponds to a MRT data segment 53 (indicated in FIG. 3 using a dashed line). In FIG. 3, a plurality of eight MRT data segments 53 is needed to sample an entire slice of the k-space 50; in other words, the MRT data segment 53 relates to a subset of all k-space samples 52. However, it should be understood that in various embodiments a smaller or larger number of samples 52 may relate to a single MRT data segment 53. For example, it is possible that a MRT data segment 53 contains all samples 52 having the same slice encoding, i.e., correspond to an entire slice of the k-space 50.

Different trajectories, i.e., sequences of acquired samples 52, can be used in order to acquire the MRT data. For example, such trajectories can be of statistical order, i.e. a random sequence of the samples 52, can be in order of increasing rows or columns of the k-space 50, can relate to spiral trajectories starting from the k-space center 51, or can relate to radial progression away from the k-space center 51. Various techniques are known to the skilled person in order to implement such k-space trajectories, such that there is no need to discuss further details in this context.

Turning back to FIG. 1, the matching provides the associations between those PET data segments and MRT data segments 53 which are acquired during related portions of the respiratory cycle of the patient 100. For this, the processor 10 is configured as set forth above to determine the further data being indicative of the patient's respiratory cycle. Various techniques exist to determine the further data.

For example, a respiratory unit 6 can be optionally provided, for example in the form of a breathing sensor or a movement detection device, e.g., an optical and/or mechanical device. The breathing sensor can be for example a cushion-formed sensor being attached to the patient 100 and measuring a movement of the patient's 100 lung 102 (cf. FIG. 2). The movement detection device can also be a camera or the like monitoring a movement of the patient's chest. The respiratory unit 6 can be configured to repeatedly measure indicative values, e.g. at a fixed rate. When monitoring the cardiac cycle, a cardiac unit (not shown in FIG. 1) may be provided instead of the respiratory unit 6. The processor 10 can be configured to determine the further data based on this repeatedly measured indicative value during the first and second imaging periods.

However, in various further embodiments it is not necessary to provide the separate respiratory unit 6. Rather, the MRT imaging unit 7 can be configured to measure navigator MRT data being indicative of a motion of the lung 102 of the patient, e.g., by acquiring the MRT data for a comparably small region containing a portion of the patient's diaphragm 102. In case the cardiac cycle is monitored, navigator MRT data for a position of the patient's heart may be acquired. For example, the MRT imaging unit 7 can be configured to acquire the navigator MRT data in between two subsequent MRT data segments of the MRT data. Then the processor 10 can be configured to determine the further data based on the navigator MRT data.

In various further embodiments, the determining of the further data by the processor 10 can comprise obtaining the further data from the MRT data. This is because the MRT data itself can be indicative of the respiratory cycle of the patient 100. For example, the position of the organ 105 may be indicative of the respiratory cycle.

It should be understood that in response to the specific situation, e.g., the location of the region of interest 101 etc., within the patient 100 an individual selection or a combination of the various embodiments for determining the further data as set forth above may be appropriate. Averaging may be employed when a combination of the different options is implemented to obtain the further data.

Figure 5:
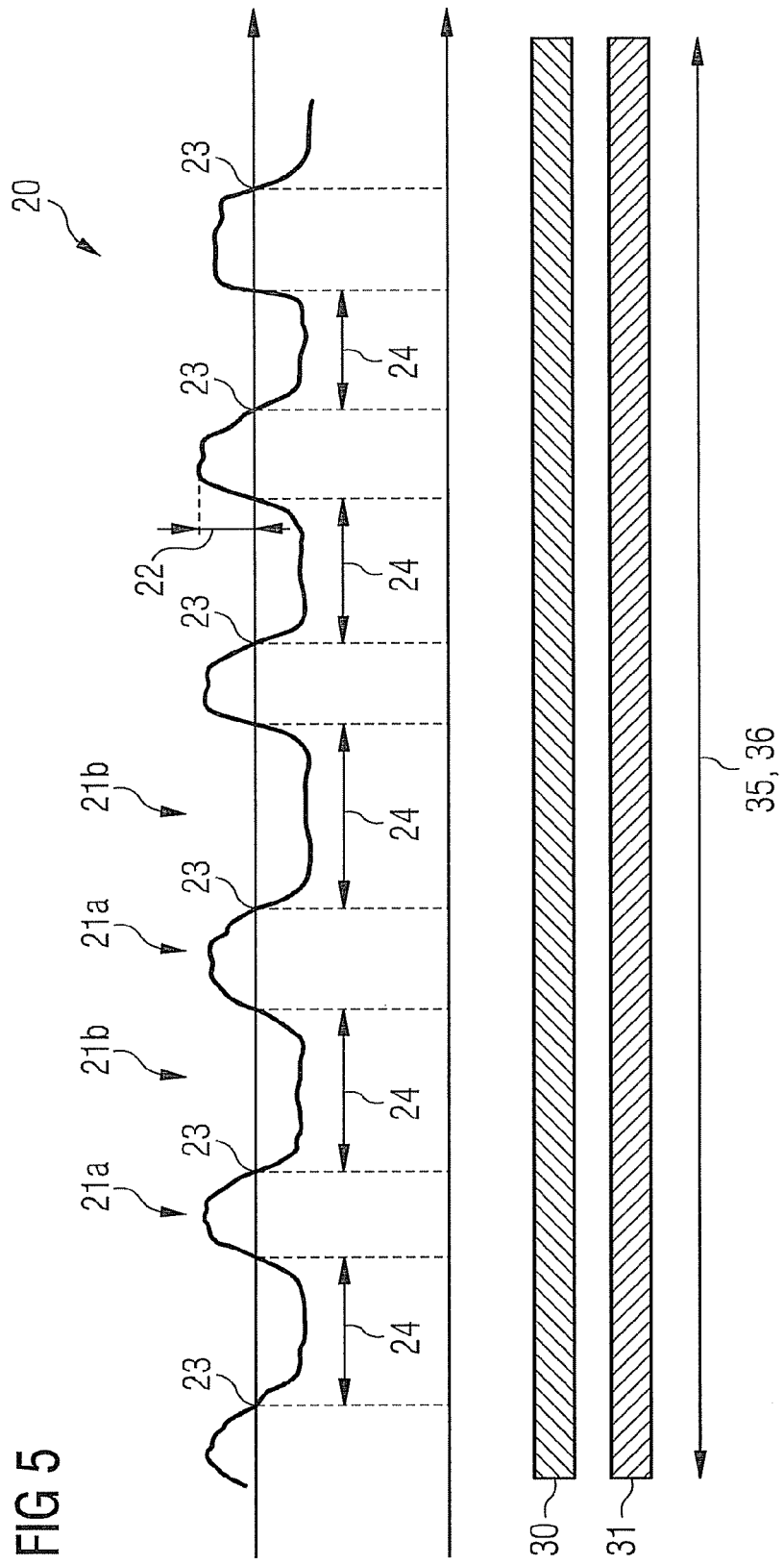
FIG. 5 illustrates the acquiring of PET data and MRT data, wherein different PET and MRT data segments are indicated with respect to the respiratory cycle, according to various embodiments of the invention.

In FIG. 5, upper part, the respiratory cycle 20 is illustrated. Indicated is, e.g., a motion of the patient's 100 diaphragm or lung 102. The respiratory cycle 20 has an amplitude 22 and phases 21a, 21b corresponding to inhalation and exhalation. Trigger events 23 mark the beginning of an exhalation phase.

In FIG. 5, lower part, the simultaneous acquiring of the PET data 30 and the MRT data 31 during the first imaging period 35 and the second imaging period 36, respectively, is illustrated.

As can be seen from FIG. 5, PET and MRT data 30, 31 is available for all phases 21a, 21b and amplitudes 22 of the respiratory cycle 20. However, when MRT data 31 which originates from different amplitudes 22 and phases 21a, 21b of the respiratory cycle 20 is used for the attenuation correction, motion artefacts and inaccuracies in the PET image can result. In other words, when performing the attenuation correction irrespective of the respiratory cycle 20 of the patient 100, the motion artefacts may result. This may degrade the accuracy of the attenuation correction. Therefore, the signal-to-noise and/or the spatial resolution of the PET data 30 may be degraded. Subsequently derived physical values, e.g., the volume of the organ 105 may be subject to larger uncertainties. For example, due to the motion of the region of interest 101 in dependence on the particular phase 21a, 21b of the respiratory cycle 20, wrong PET attenuation values 60 may be used for the attenuation correction by the processor 10 if, e.g., MRT data 31 originating from the inhalation 21a is used for attenuation correction of PET data 30 obtained during the exhalation phase 21b, etc.

According to various embodiments, the processor 10 is configured to perform the matching between the PET data 30 and the MRT data 31 with respect to the amplitude 22 and/or with respect to the phases 21a, 21b such that the matching provides association between those PET and MRT data segments which are acquired during related portions of the respiratory cycle 20, e.g., having substantially equal phases 21a, 21b and/or amplitudes 22. Then the processor 10 is configured to apply the attenuation correction to the PET data 30 such that the attenuation correction for a given PET data segment is based on the respective associated at least one MRT data segment 53 obtained from the matching.

In order to provide the matching between related phases 21a, 21b of the respiratory cycle 20, gating may be applied to the PET and MRT data 30, 31. Various gating techniques can be employed, such as self-gating, retrospective gating, and prospective gating and semi-prospective gating. In principle, all such techniques rely on using MRT and PET data 30, 31 having substantially equal phases 21a, 21b of the respiratory cycle 20. Therefore, in other words, the gating of the PET and MRT data 30, 31 may be employed such that the matching provides the associations under the constraint of related phases 21a, 21b of the respiratory cycle 20. The gating is illustrated in FIG. 6.

Figure 6:
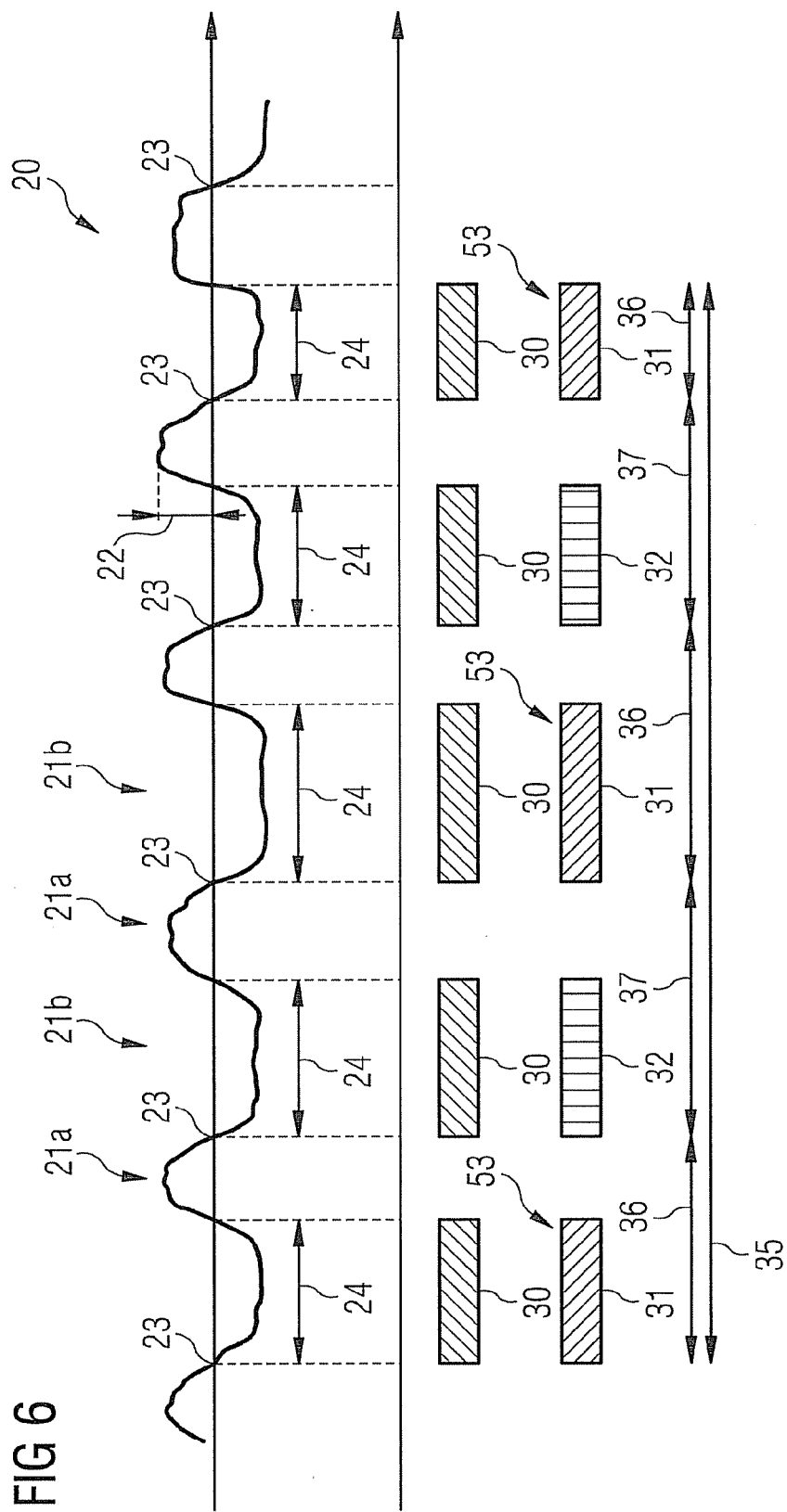
FIG. 6 illustrates the acquiring of PET data and MRT data, wherein different PET and MRT data segments are indicated with respect to the respiratory cycle, according to various further embodiments of the invention.

As can be seen from FIG. 6, PET and MRT data 30, 31 is only acquired during gating periods 24 which correspond to the exhalation phase 21b of the respiratory cycle 20. By such prospective gating, the further data being indicative of the respiratory cycle 20 is analyzed in real time and/or on-the-fly by a gating unit 9 (cf. FIG. 1); the further data is indicative of the trigger event 23 marking the beginning of the exhalation phase 21b. The control unit 11 can be configured to synchronize the acquiring of the PET and MRT data 30, 31 during the gating periods 24 in response to the trigger event 23.

However, in various other embodiments, it may be possible to continuously acquire the PET and MRT data 30, 31 and retrospectively selectively discard those PET and MRT data segments which have be previously acquired outside the gating periods 24. Such a situation may be applied to the PET and MRT data 30, 31 as depicted in FIG. 5. For example, in such a retrospective gating scheme, it is possible to determine the further data from the MRT data 31 itself. In such a case, self-gated PET and MRT data 30, 31 may be obtained. This may be advantageous, as no separate respiratory unit 6 may be necessary.

Figure 7:
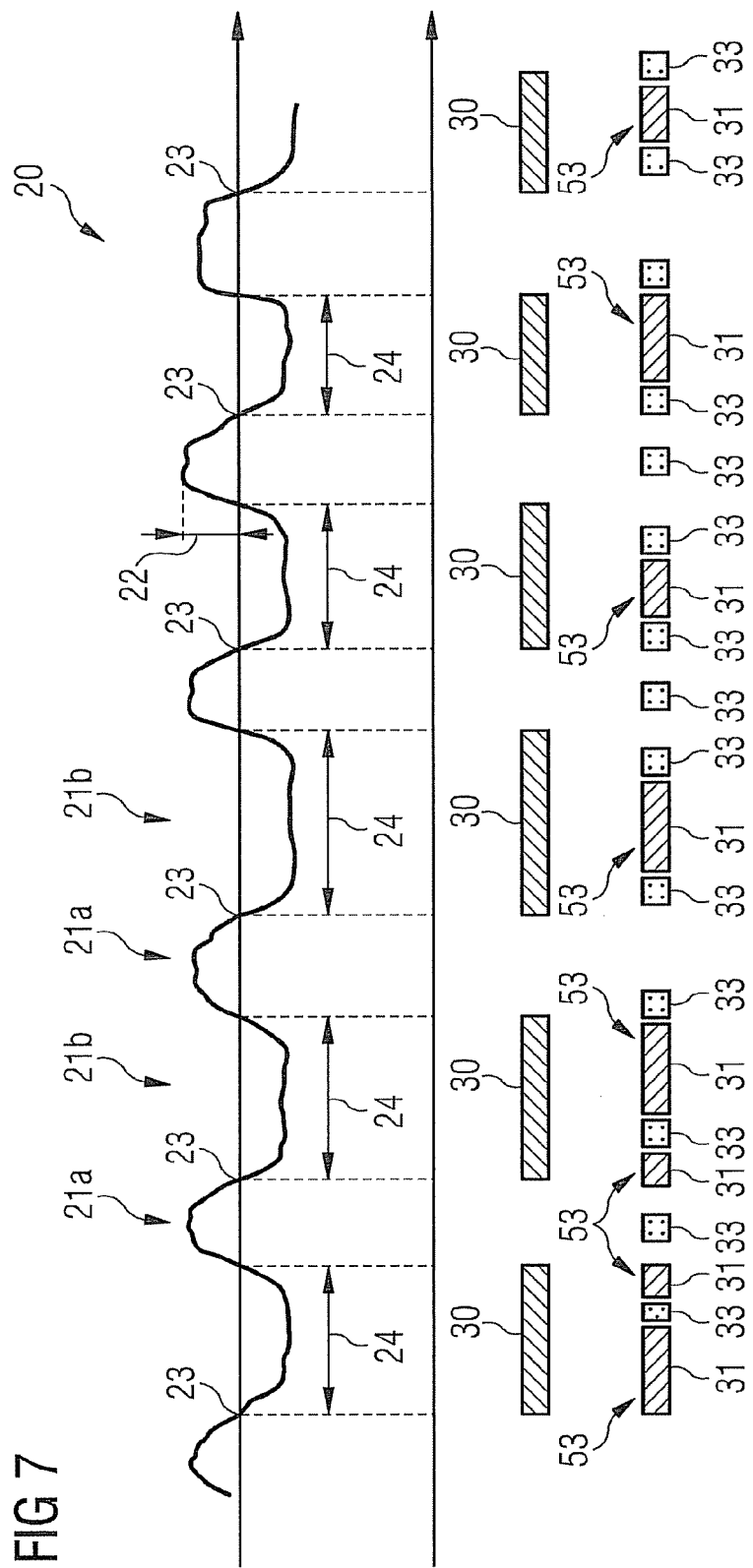
FIG. 7 illustrates the acquiring of PET data and MRT data, wherein different PET and MRT data segments are indicated with respect to the respiratory cycle, according to various further embodiments of the invention where navigator MRT data is used.

Illustrated in FIG. 7 is a situation comparable to the situation in FIG. 6; however, interleaved with the MRT data 31 is navigator MRT data 33. The navigator MRT data 33 is indicative of a motion of the lung 102 of the patient 100 and is measured by the MRT imaging unit 7 in between two subsequent MRT data segments. For example, the imaging sequence used to measure the navigator MRT data 33 can rely on a PPA imaging sequence, such as GRAPPA, employing a large acceleration factor and, e.g. imaging solely a single slice. By such device(s), it can be possible that the average duration of the acquiring of the navigator MRT data 33 is comparably short, in particular if compared to the acquiring of the MRT data segments 53.

While in FIG. 7 the measuring of the navigator MRT data is interleaved with the MRT data 31—and therefore the time periods available for the measuring are determined by the acquiring of the MRT data 31—in another embodiment it is possible the navigator MRT data 33 is measured at a fixed repetition rate.

Turning back to FIG. 6, depicted in FIG. 6 is further MRT data 32. The further MRT data 32 is acquired interleaved in between two subsequent MRT data segments 53 of the MRT data 31. For example, the further MRT data 32 can be used for a diagnostic application other than the attenuation correction. The further MRT data 32 is acquired during a third imaging period 37. In particular, the third imaging period 37 is a fraction of the first imaging period 35 and is complementary to the second imaging period 36.

Figure 8:
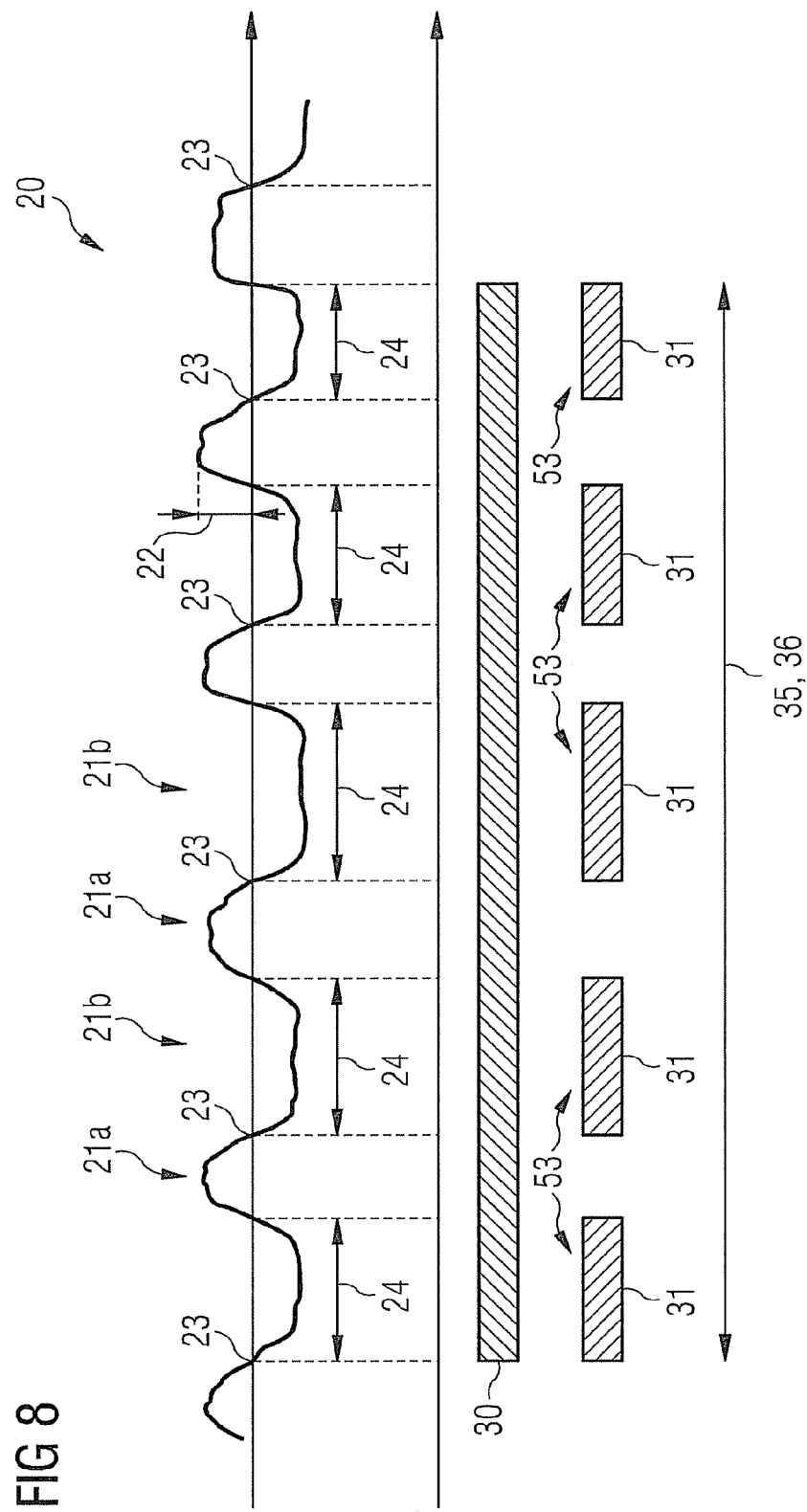
FIG. 8 illustrates the acquiring of PET data and MRT data, wherein different PET and MRT data segments are indicated with respect to the respiratory cycle, according to various further embodiments of the invention.

Illustrated in FIG. 8 is a further case, where the PET data 30 is continuously acquired with no prospective gating, and only retrospective gating is acquired to the PET data 30 (not shown in FIG. 8). However, prospective gating is applied to the MRT data 31. Various combinations between prospective and retrospective gating, as well as self-gating, can be applied to the PET and MRT data 30, 31. It should further be understood that the further MRT data 32 does not need to obey the same gating scheme as applied to the PET and MRT data 30, 31. This is because the diagnostic application of the further MRT data 32 can be independent of the respiratory cycle 20 of the patient 100. In particular, if the diagnostic application of the further MRT data 32 is independent of the PET data 30, it is not necessary to ensure synchronously gating the PET data 30 and the further MRT data 32.

The gating as discussed above allows that the matching provides the associations between PET and MRT data segments relating to substantially the same phases 21a, 21b of the respiratory cycle. In the following, techniques will be explained which allow that the matching provides the associations between PET and MRT data segments relating to substantially the same amplitudes 22.

Figure 9:
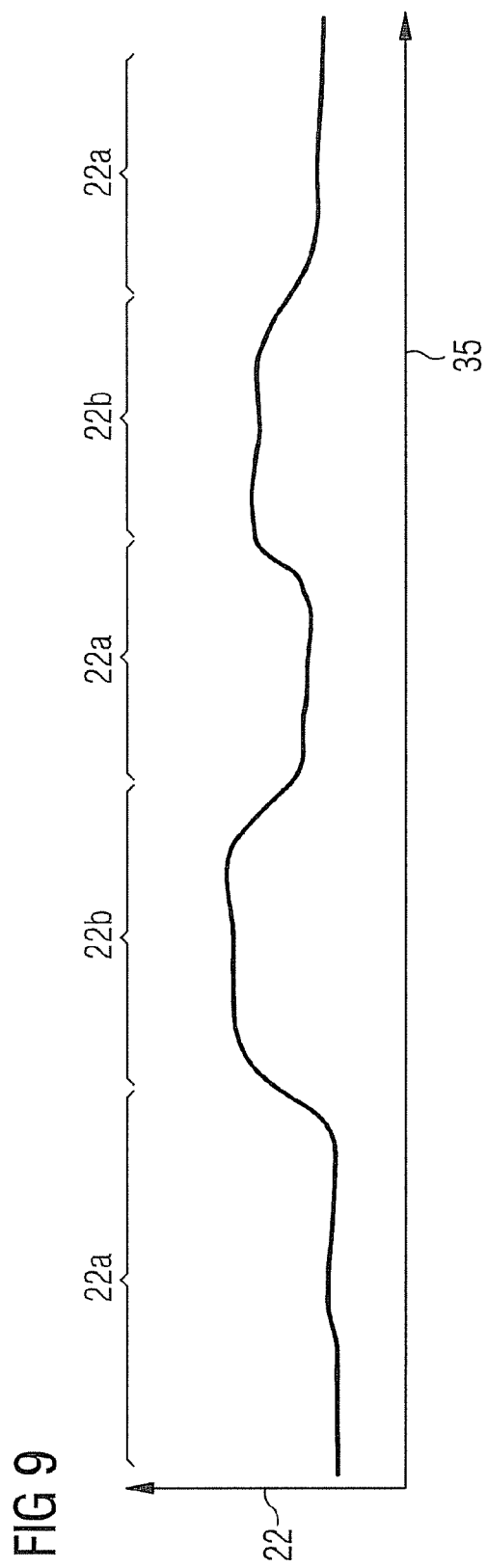
FIG. 9 illustrates an amplitude of the patient's respiratory cycle over time.

In FIG. 9, the amplitude 22 of the respiratory cycle 20 is plotted over time. As can be seen from FIG. 9, the amplitude 22 remains substantially constant during extended periods of time corresponding to short breathing 22a (small amplitude 22) and deep breathing 22b (large amplitude 22). In particular, these time intervals of substantially constant amplitude 22 may cover a larger number of full cycles of the respiratory cycle 20. In other words, the characteristic time scale of a change of the amplitude 22 may be considerably longer than a duration of a period of the respiratory cycle 20.

A similar argumentation may apply to the cardiac cycle with respect to heartbeat frequency and blood pressure.

Therefore, in various embodiments, the PET data segments and the MRT data segments may be respectively provided with timestamps being indicative of a time of the acquiring of the PET and MRT data segment. The processor 10 then is configured to provide the associations between the PET and MRT data segments based on a difference of the respective timestamps such that the PET and MRT data segments have related amplitudes 22 of the respiratory cycle 20. For example, the processor 10 can be configured to provide the associations between those PET and MRT data segments which have a minimized or minimum difference of the respective timestamps under the constraint of related phases of the respiratory cycle 20. Because the rate of change of the amplitude 22 of the respiratory cycle 20 is comparably small if compared to the time intervals of the acquiring of subsequent PET and MRT data segments, by matching those PET and MRT data segments which have a small difference of the time stamps, substantially equal amplitudes 22 may be achieved.

In various further embodiments, the processor 10 is configured to determine the amplitude 22 of the respiratory cycle 20 based on the further data. The processor 10 then is configured to match those PET and MRT data segments which have a minimum difference of the respective explicitly determined amplitudes 22 of the respiratory cycle 20, optionally under the constraint of related phases 21a, 21b of the respiratory cycle 20. In such a scenario, it may be possible to match also such PET and MRT data segments which have a comparably longer time difference between the respective acquisitions. There may further be no need to provide the timestamps. This may enable to acquire the MRT data 31, e.g., only in the beginning or end of the acquiring of the PET data 30.

Figure 10:
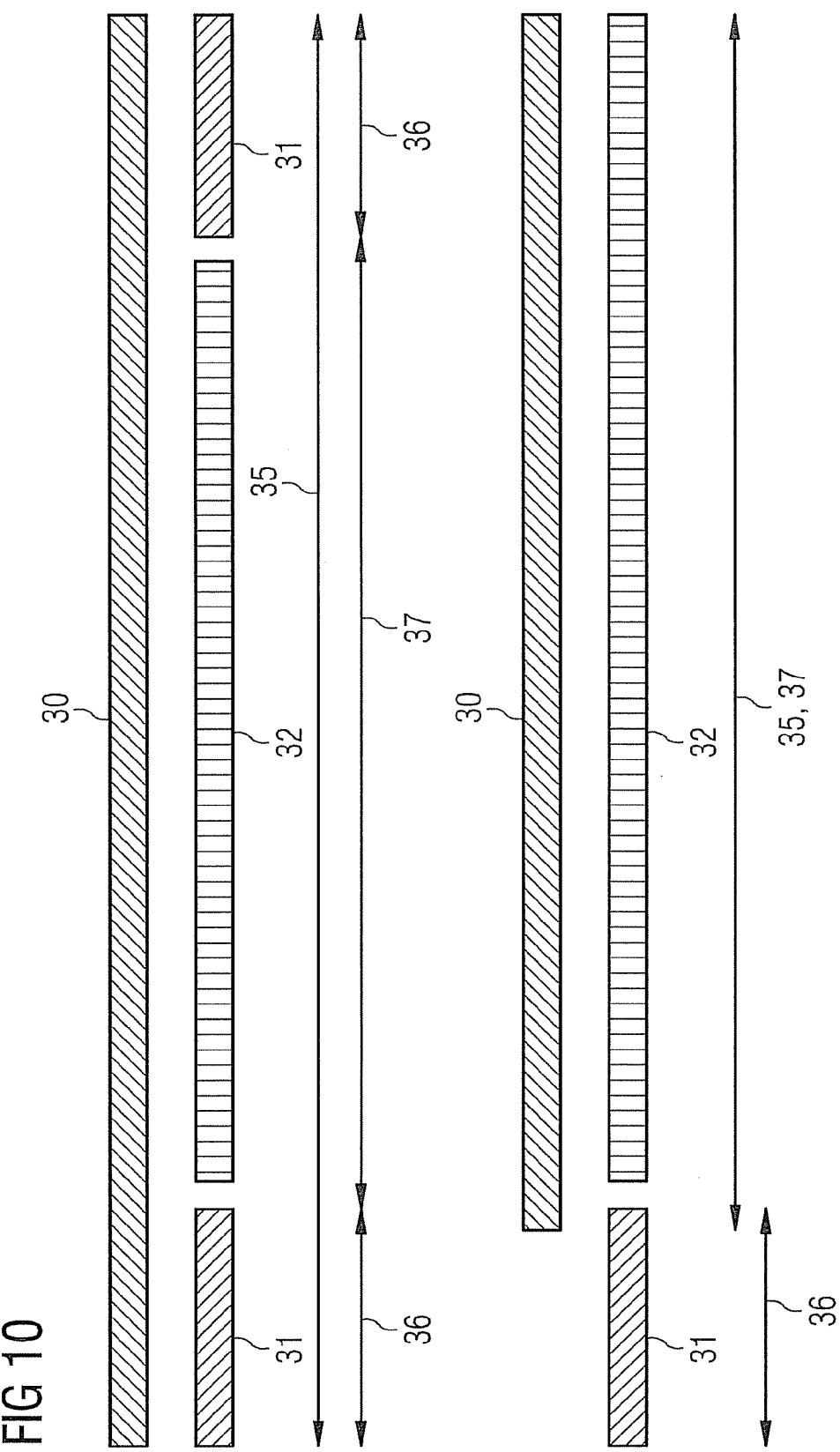
FIG. 10 illustrates the temporal arrangement of a first imaging period corresponding to the acquiring of the PET data, a second imaging period corresponding to the acquiring of the MRT data, and a third imaging period corresponding to the acquiring of further MRT data for a diagnostic application.

Such scenarios, i.e., approaches of arranging the first and second and third imaging periods 35, 36, 37, are illustrated in FIG. 10. Illustrated in FIG. 10, upper part, is a situation, where the MRT data 31 is only acquired during the beginning and the ending of the acquiring of the PET data 30. In other words, the second imaging period 36 is a small fraction of the first imaging period 35. In between and during the third imaging period 37, the further MRT data 32 for the diagnostic application is acquired. Typically, the integration times for the acquisition of the PET data 30 are much longer than the integration times necessary to obtain the MRT data 31 for significant attenuation correction. Therefore, the excess of time can be used in order to determine the further MRT data 32.

In FIG. 10, lower part, a similar situation is shown. However, the second imaging period 36 only has a small overlap with the first imaging period 35. In other words, the MRT data 31 is acquired during a pre-scan before the acquiring of the PET data 30. Various other embodiments with respect to the arrangement of the imaging period 35, 36, 37 are conceivable. FIG. 10 must therefore not be construed as being limiting.

Above, the matching has been discussed with respect to related portions of the respiratory cycle 20, i.e., phase 21a, 21b and amplitude 22. However, the matching may need to fulfil also requirements with respect to the MRT image 31a. Namely, it should be possible to calculate the MRT image 31a from the MRT data 31, i.e., the k-space 50 should be sufficiently sampled such that a signal-to-noise ratio of the MRT image 31a becomes acceptable. To this respect, the processor 10 is configured to provide the matching such that a MRT image can be calculated from the associated at least one MRT data segment 53. Then the processor is configured to calculate the MRT image 31a from the associated at least one MRT data segment 53.

For example, the MRT imaging unit 7 can be configured to randomly or statistically acquire the k-space samples 52, e.g., with a higher sampling probability close to the k-space center 51. Moreover, the MRT imaging unit 7 can be configured to redundantly sample the k-space 50, i.e., to provide multiple measurement values for each sample 52. In such a case, when applying retrospective gating, the likelihood of not loosing all values for a particular k-space sample 52 due to the selectively discarding can be increased. Then it may be possible that the matching provides the associations for a sufficient amount of MRT data segments 53 such that the entire k-space 50 is covered.

While the various elements 1-13 of FIG. 1 have been introduced as separate elements, it should be understood that some of these elements are optional elements, e.g., the respiratory unit 6, while other elements can be combined as hardware and/or software with each other into a single unit. For example, the PET and MRT imaging units 7, 8 may be integrated as a single processing device, e.g. as software elements. Also, the control unit 11 may be integrated as software on the single processing device.

Illustrated in FIG. 11 is a flowchart of a method of attenuation correction according to various embodiments of the present invention. The method starts in step S1. In step S2, the patient 100 is positioned on the table 5 in the combined PET-MRT system 1.

Next, in step S3, the PET data 30 and the MRT data 31 is acquired during the first and second imaging period 35, 36, respectively. The PET data 30 comprises a plurality of PET data segments and is acquired by the PET imaging unit 8. Respectively, the MRT data comprises a plurality of MRT data segments 53 and is acquired by the MRT imaging unit 7. Furthermore, in step S3, the further data being indicative of the respiratory cycle 20 of the patient 100 is determined by the processor 10. For example, the determining can comprise measuring of the further data, e.g., by the respiratory unit 6 or by way of the MRT imaging unit 7. For example, the MRT imaging unit can acquire the navigator MRT data 33. In a further embodiment, it is also possible that the further data is obtained from the MRT data 31.

In step S4, the PET data segments and the MRT data segments 53 are matched based on the further data. The matching provides associations between respective PET data segments and at least one MRT data segment having substantially equal phases 21a, 21b of the respiratory cycle 20 and/or substantially equal amplitudes 22 of the respiratory cycle 20. Furthermore, in step S4, the matching occurs such that from the at least one MRT data segment which is associated with each PET data segment, the MRT image 31a can be calculated. This, in other words, corresponds to providing sufficient samples 52 of the k-space 50.

Then, in step S5, the MRT image 31a is calculated from the matched at least one MRT data segment for each PET data segment. The MRT image 31a corresponds to the μ-map of the attenuation value. In step S6, the attenuation correction is applied to the PET data 30 based on the respective MRT images 31a. In particular, for each PET data segment, the respectively matched MRT image 31a can be used in order to apply the attenuation correction.

In step S7, the attenuation corrected PET image is provided based on the corrected PET data as obtained from step S6. The method ends in step S8.

FIGS. 12 and 13 illustrate the acquiring of the PET and MRT data 30, 31 in further detail. In FIG. 12, a prospective gating scheme is applied to, both, the acquiring of the PET and MRT data 30, 31. First, in step T1 it is checked whether a trigger event 23 is indicated in the further data.

Once a trigger event 23 is detected, in steps T2 and T3, PET and MRT data 30, 31 is synchronously, i.e. in parallel, acquired within the respective gating period 24 and provided with a timestamp. The timestamp is indicative of a time of the execution of the steps T2 and T3. The timestamp can be subsequently employed to provide the associations between the PET and MRT data 30, 31 as discussed with reference to FIG. 9 above. The PET data 30 acquired in step T2 can comprise a number of PET events detected via the PET detector 4. Each of these PET events can correspond to a single PET data segment; in another embodiment it is also possible that all the PET events acquiring during the step T2 of FIG. 12 are grouped into a single PET data segment. This may depend on the granularity which is desired for the attenuation correction of steps S4-S6 of FIG. 11.

Respectively, during step T3, a predefined number of k-space samples 52 are acquired as a MRT data segment 53. For example, during step T3, a sufficient number of k-space samples 52 is acquired to calculate an entire MRT image 31a. This can be achieved by choosing a density of the k-space samples 52 accordingly and/or setting an acceleration factor of a PPA MRT imaging sequencing image accordingly. However, it is also possible that the MRT data segment 53 acquired during the step T3 of FIG. 12 only corresponds to a subset of all k-space samples 52 of the entire k-space 50, e.g., with a single slice encoding.

To this respect, in step T4, it is checked if further PET data and/or MRT data is needed. In case for the data it is needed, the steps T1, T2, T3 are executed anew. Further data can be needed if for example not the entire k-space 50 has been sufficiently sampled during the previous step T3. Furthermore, in step T4 it can be checked whether a lower threshold for the first and/or second imaging periods 35, 36 has been reached. Such lower thresholds may correspond to a required minimum signal-to-noise ratio of the PET image and MRT image 31a, respectively.

In case it is decided in step T4 that no further data is needed, the method commences with step S4 of FIG. 11.

Illustrated in FIG. 13 is an alternative embodiment of step S3, i.e., the acquiring of the PET and MRT data 30, 31. In the embodiment illustrated in FIG. 13, a prospective gating scheme is applied to the acquiring of the MRT data 31, while a retrospective gating scheme (not shown in FIG. 13) is applied to the PET data 30. Therefore, during the execution of the steps U1, U3, U4, which correspond to the steps T1, T3, T4 of FIG. 12, the PET data 30 is continuously acquired. Only in step U5, i.e., after finishing the acquisition/after the first and second imaging periods 35, 36, those PET data segments are selectively discarded which have been acquired in step U2 outside the gating periods 24.

It should be understood that modifications to the embodiments shown in FIGS. 12 and 13 can be implemented. For example, it can be possible to prospectively gate the acquiring of the PET data 30 and retrospectively gate the acquiring of the MRT data 31. It can also be possible to retrospectively gate, both, the acquiring of the PET and MRT data 30, 31, etc.

When acquiring the PET and MRT data 30, 31 in steps T2, T3 of FIG. 12, and in steps U2, U3 in FIG. 13, it is optionally possible to provide the respective PET and MRT data 30, 31 with timestamps. The timestamps can be used, as is illustrated in FIG. 14, with respect to the matching: by providing associations between those MRT and PET data segments which have a minimized difference of timestamps, substantially equal amplitudes 22 of the respiratory cycle 20 can be achieved for the matched PET and MRT data (cf. FIG. 9).

FIG. 14 illustrates step S4 of FIG. 11 in further detail. First, in step V1, a given PET data segment is selected, e.g. a single PET event or a number of PET events. In step V2, a set of MRT k-space samples 52 is associated with the selected PET data segment of step V1 as associated MRT data segment 53. The processor 10 is configured to perform this matching such that the difference of the respective timestamps of the PET and MRT data segments is small; alternatively or additionally, the matching is performed by the processor such that the associated MRT and PET data segments have a small difference of the amplitude 22 of the respiratory cycle 20. As the PET and MRT data segments which are associated in step V2 originate from a gated acquisition as set forth with respect to the FIGS. 12 and 13 above, they have substantially equal phases 21a, 21b and amplitudes 22 of the respiratory cycle 20.

Next, in step V3, it is checked whether further k-space samples 52 are needed in order to reconstruct the MRT image 31a. If further k-space samples 52 are needed, i.e., if the k-space 50 is not sufficiently sampled by the associated MRT data segments 53 obtained from step V2, step V2 is executed anew and further MRT data segments are associated with the selected PET data segment of step V1. By this device(s), at least one MRT data segment is associated with the selected PET data segment of step V1.

Once the sufficient number of MRT data segments is associated with the selected PET data segment of step V1, in step V4 it is checked whether a further PET data segment exists. In the affirmative, the steps V1, V2, V3 are executed anew with the further PET data segment being selected. To this respect, it should be understood that one and the same MRT data segment may be associated with more than one PET data segment.

Although the invention has been shown and described with respect to certain preferred embodiments, equivalents and modifications will occur to others skilled in the art upon the reading and understanding of the specification. For example, throughout the text, reference has been predominantly made to the iterative cycle of the physiological observable being the respiratory cycle of the patient. However, it should be understood that equivalent techniques may be applied to the iterative cycle being the cardiac cycle or any other repetitive physiological observable, such as the swallowing reflex etc. The present invention includes all such equivalents and modifications and is limited only by the scope of the appended claims.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of attenuation correction of Positron Emission Tomography (PET) data based on Magnetic Resonance Tomography (MRT) data using a combined PET-MRT system, the PET data and the MRT data being acquired for a region of interest of a patient, the method comprising:
   acquiring the PET data for the region of interest by a PET imaging unit during a first imaging period, the PET data comprising a plurality of PET data segments;
   acquiring the MRT data for the region of interest and a surrounding region, by a MRT imaging unit, during a second imaging period, the MRT data comprising a plurality of MRT data segments, the first and second imaging periods at least partially overlapping;
   determining, by a processor, further data being indicative of an iterative cycle of a physiological observable of the patient;
   matching, by the processor, the PET data with the MRT data, based on the further data, to provide associations between each PET data segment and at least one MRT data segment which are acquired during related portions of the iterative cycle;
   applying, by the processor, the attenuation correction to the PET data based on the MRT data, wherein the attenuation correction is based on the provided associations; and
   providing the attenuation corrected PET data to a display.

2. The method of claim 1, wherein the related portions of the iterative cycle include at least one of related phases of the iterative cycle and related amplitudes of the iterative cycle.

3. The method of claim 2, wherein
   the second imaging period is a fraction of the first imaging period,
   each PET data segment includes a timestamp indicative of a time of the acquiring of the respective PET data segment,
   each MRT data segment includes a timestamp indicative of a time of the acquiring of the respective MRT data segment, and
   the matching provides the associations between each PET data segment and the at least one MRT data segment based on a difference of the respective timestamps such that the associated PET and MRT data segments have the related amplitudes of the iterative cycle.

4. The method of claim 3, wherein the matching provides the associations between PET and MRT data segments having a minimized difference between the respective timestamps under the constraint of related phases of the iterative cycle.

5. The method of claim 2, further comprising:
   determining the amplitudes of the iterative cycle based on the further data, wherein the matching provides the associations between PET and MRT data segments having a minimized difference between the respective amplitudes of the iterative cycle under the constraint of related phases of the iterative cycle.

6. The method of claim 1, wherein the matching provides the associations such that a MRT image is calculatable from an associated at least one MRT data segment, wherein the method further comprises:
calculating the MRT image from the associated at least one MRT data segment, wherein the MRT image provides a segmentation of the region of interest and the surrounding region based on PET attenuation values, and
wherein the applying of the attenuation correction is based on the PET attenuation values.

7. The method of claim 1, wherein the MRT data segments comprise a subset of all k-space samples or all k-space samples and wherein the PET data segments comprise a single PET event.

8. The method of claim 1, wherein the acquiring the MRT data comprises:
at least one of repeatedly sampling the region of interest and the surrounding region for a plurality of iterations and using a statistical sequence.

9. The method of claim 1, further comprising:
acquiring further MRT data for a diagnostic application during a third imaging period by the MRT imaging unit, the third imaging period being a fraction of the first imaging period and being complementary to the second imaging period.

10. The method of claim 1, wherein the iterative cycle of the physiological observable is a respiratory cycle of the patient or a cardiac cycle of the patient.

11. A combined PET-MRT system configured to perform the method of attenuation correction of claim 1, wherein the combined PET-MRT system includes the PET imaging unit, the MRT imaging unit and the processor.

12. A method of attenuation correction of Positron Emission Tomography (PET) data based on Magnetic Resonance Tomography (MRT) data using a combined PET-MRT system, the PET data and the MRT data being acquired for a region of interest of a patient, the method comprising:
acquiring the PET data for the region of interest by a PET imaging unit during a first imaging period, the PET data comprising a plurality of PET data segments;
acquiring the MRT data for the region of interest and a surrounding region, by a MRT imaging unit, during a second imaging period, the MRT data comprising a plurality of MRT data segments, the first and second imaging periods at least partially overlapping;
determining, by a processor, further data being indicative of an iterative cycle of a physiological observable of the patient;
matching, by the processor, the PET data with the MRT data, based on the further data, to provide associations between each PET data segment and at least one MRT data segment which are acquired during related portions of the iterative cycle; and
applying, by the processor, the attenuation correction to the PET data based on the MRT data, wherein the attenuation correction is based on the provided associations
gating the PET data and the MRT data to phases of the iterative cycle by a gating unit such that the associated PET data segments and at least one MRT data segment are acquired during related phases of the iterative cycle, the gating being based on the determined further data.

13. The method of claim 12, wherein the determining the further data comprises:
repeatedly measuring the further data during the first imaging period and the second imaging period.

14. The method of claim 13, further comprising:
measuring the further data in between two subsequent MRT data segments, wherein the further data is navigator MRT data.

15. The method of claim 12, wherein the determining the further data comprises:
obtaining the further data from the MRT data to obtain self-gated PET and MRT data.

16. The method of claim 12, wherein the gating comprises:
selectively discarding of the PET data segments and the MRT data segments which are acquired outside gating periods.

17. The method of claim 12, wherein the gating comprises:
enabling the acquiring of the MRT data and PET data during gating periods,
wherein the acquiring the MRT data yields a number of k-space samples as MRT data segments of the plurality of MRT data segments during each gating period.

18. The method of claim 12, wherein the gating comprises a semi-prospective gating scheme.

19. A combined PET-MRT system for acquiring, for a region of interest of a patient, MRT data and PET data and for providing attenuation correction of the PET data based on the MRT data, the combined PET-MRT system comprising:
a PET imaging unit configured to acquire the PET data for the region of interest during a first imaging period, the PET data comprising a plurality of PET data segments;
an MRT imaging unit configured to acquire the MRT data for the region of interest and a surrounding region during a second imaging period, the MRT data comprising a plurality of MRT data segments, wherein the first and second imaging periods at least partially overlap; and
a processor configured ton
determine further data being indicative of an iterative cycle of a physiological observable of the patient,
match the PET data with the MRT data, based on the further data, to provide associations between each PET data segment and at least one MRT data segment which are acquired during related portions of the iterative cycle, and
apply the attenuation correction to the PET data is based on the MRT data, wherein the attenuation correction is based on the provided associations.

20. A computer readable medium including program segments for, when executed on a computer device, causing the computer device to,
acquire Positron Emission Tomography (PET) data for a region of interest of a patient by a PET imaging unit during a first imaging period, the PET data including a plurality of PET data segments;
acquire Magnetic Resonance Tomography (MRT) data for the region of interest and a surrounding region, by a MRT imaging unit, during a second imaging period, the MRT data including a plurality of MRT data segments, the first and second imaging periods at least partially overlapping;
determine further data being indicative of an iterative cycle of a physiological observable of the patient;
match the PET data with the MRT data, based on the further data, to provide associations between each PET data segment and at least one MRT data segment which are acquired during related portions of the iterative cycle;

apply the attenuation correction to the PET data based on the MRT data, wherein the attenuation correction is based on the provided associations; and provide the attenuation corrected PET data to a display.

* * * * *